(12) United States Patent
Hemnes et al.

(10) Patent No.: US 9,687,176 B2
(45) Date of Patent: Jun. 27, 2017

(54) ORAL END TIDAL CARBON DIOXIDE PROBE FOR DIAGNOSING PULMONARY ARTERIAL HYPERTENSION

(75) Inventors: Anna R. Hemnes, Nashville, TN (US); Alexander Newman, Nashville, TN (US); John Newman, Nashville, TN (US)

(73) Assignee: VANDERBILT UNIVERSITY, Nashville, TN (US)

(*) Notice: Subject to any disclaimer, the term of this patent is extended or adjusted under 35 U.S.C. 154(b) by 1110 days.

(21) Appl. No.: 13/448,095

(22) Filed: Apr. 16, 2012

(65) Prior Publication Data

US 2012/0302908 A1 Nov. 29, 2012

Related U.S. Application Data

(63) Continuation-in-part of application No. 12/578,841, filed on Oct. 14, 2009, now abandoned.

(60) Provisional application No. 61/476,133, filed on Apr. 15, 2011, provisional application No. 61/106,066, filed on Oct. 16, 2008.

(51) Int. Cl.
*A61B 5/08* (2006.01)
*A61B 5/083* (2006.01)
*A61B 5/097* (2006.01)

(52) U.S. Cl.
CPC ............ *A61B 5/082* (2013.01); *A61B 5/0836* (2013.01); *A61B 5/097* (2013.01)

(58) Field of Classification Search
CPC ........ A61B 5/082; A61B 5/097; A61B 5/0836
See application file for complete search history.

(56) References Cited

U.S. PATENT DOCUMENTS

| 5,293,875 A * | 3/1994 | Stone ........................... 600/532 |
| 6,200,271 B1 | 3/2001 | Kück et al. |
| 2004/0236240 A1 | 11/2004 | Kraus et al. |
| 2007/0068810 A1 | 3/2007 | Tsukashima et al. |
| 2007/0068811 A1 | 3/2007 | Tsukashima et al. |

(Continued)

FOREIGN PATENT DOCUMENTS

| WO | 2010045295 A1 | 4/2010 |
| WO | 2010135513 A1 | 11/2010 |

(Continued)

OTHER PUBLICATIONS

Anderson et al. (Association of high resting end tidal CO2 with carotid artery thickness in women, but not men, Journal of Hypertension, 2001, vol. 19 No. 3, pp. 459-463).*

(Continued)

*Primary Examiner* — Michael Kahelin
*Assistant Examiner* — Tho Tran
(74) *Attorney, Agent, or Firm* — GTC Law Group PC & Affiliates

(57) ABSTRACT

This disclosure concerns improved capabilities for evaluating pulmonary arterial hypertension (PAH). A system and method of evaluating PAH in a subject may include measuring end tidal partial pressure of exhaled carbon dioxide in the subject, wherein the measurement is made orally using described systems or devices. Integrated sensors enable the measurement and characterization of other respiratory gas components, some of which may be indicative of disease. The system and method can be used to monitor a course of treatment for PAH.

16 Claims, 33 Drawing Sheets

(56) References Cited

U.S. PATENT DOCUMENTS

| | | | |
|---|---|---|---|
| 2007/0129646 A1 | 6/2007 | Heinonen et al. | |
| 2010/0016750 A1* | 1/2010 | Anderson et al. | ............ 600/532 |
| 2010/0099999 A1 | 4/2010 | Hemnes et al. | |

FOREIGN PATENT DOCUMENTS

| | | |
|---|---|---|
| WO | 2012142608 A2 | 10/2012 |
| WO | 2012142608 A3 | 1/2013 |

OTHER PUBLICATIONS

Arena et al., The Partial Pressure of Resting End-Tidal Carbon Dioxide Predicts Major Cardiac Events in Patients with Systolic Heart Failure, Am Heart J., Aug. 2008. pp. 982-988).*

American Thoracic Society, , "ATS statement: guidelines for the six-minute walk test", vol. 166, Mar. 2002, pp. 111-117.

Arkles, Jeffrey S. et al., "Shape of the right ventricular Doppler envelope predicts hemodynamics and right heart function in pulmonary hypertension", Am. J. Respir. Crit. Care Med., vol. 183, 2011, pp. 268-276.

Badesch, David B. , "Diagnosis and Assessment of Pulmonary Arterial Hypertension", J. Am. Coll. Cardiol., vol. 54, 2009, pp. S55-S66.

Hansen, James E. et al., "Mixed-Expired and End-Tidal CO2 Distinguish Between Ventilation and Perfusion Defects During Exercise Testing in Patients With Lung and Heart Diseases", CHEST, vol. 132, No. 3, Sep. 2007, pp. 977-983.

Hemnes, A. R. et al., "Assessment of pulmonary vasculature and right heart by invasive haemodynamics and echocardiography", Int J Clin Pract Suppl, v. 63, (Suppl 162), Sep. 2009, pp. 4-19.

Hemnes, A. R. et al., "Bedside end-tidal CO2 tension as a screening tool to exclude pulmonary embolism", Eur Respir J, vol. 35, 2010, pp. 735-741.

Her, Charles et al., "Increased Pulmonary Venous Resistance in Morbidly Obese Patients without Daytime Hypoxia: Clinical Utility of the Pulmonary Artery Catheter", Anesthesiology, vol. 113, 2010, pp. 552-559.

Hyduk, Alexandra et al., "Pulmonary hypertension surveillance—United States, 1980-2002", MMWR, Surveillance Summaries, vol. 54(SS05), Nov. 11, 2005, pp. 1-28.

Lappas, Demetrios et al., "Indirect measurement of left-atrial pressure in surgical patients—pulmonary-capillary wedge and pulmonary-artery diastolic pressures compared with left-atrial pressure", Anesthesiology, vol. 38, No. 4, Apr. 1973, pp. 394-397.

Matsumoto, Akihiro et al., "End-tidal CO2 Pressure Decreases During Exercise in Cardiac Patients Association With Severity of Heart Failure and Cardiac Output Reserve", Journal of the American College of Cardiology, vol. 36, 2000, pp. 242-249.

McLaughlin, Vallerie V. et al., "ACCF/AHA 2009 Expert Consensus Document on Pulmonary Hypertension: A Report of the American College of Cardiology Foundation Task Force on Expert Consensus Documents and the American Heart Association Society, Inc. and the Pulmonary Hypertension Assoc.", Journal of the American College of Cardiology, vol. 53, No. 17, 2009, pp. 1573-1619.

Methvin, Amanda B. et al., "Iatory Ineffi ciency Refl ects Right Ventricular Dysfunction in Systolic Heart Failure", CHEST, vol. 139(3), 2011, pp. 617-625.

Oudiz, Ronald J. et al., "Cardiopulmonary Exercise Testing and Six-Minute Walk Correlations in Pulmonary Arterial Hypertension", Am J Cardiol, vol. 997, 2006, pp. 123-126.

Parfrey, Patrick S. et al., "Contrast material-induced renal failure in patients with diabetes mellitus, renal insufficiency, or both. A prospective controlled study.", N Engl J Med., vol. 320, No. 3, Jan. 19, 1989, pp. 143-149.

PCT/US2012/033827, , "International Application Serial No. PCT/US2012/033827, International Preliminary Report on Patentability and Written Opinion mailed Oct. 24, 2013", Vanderbilt University et al, 5 pages.

Peacock, Andrew et al., "Endpoints in pulmonary arterial hypertension: the role of clinical worsening", Curr. Opin. Pulm. Med., vol. 16, suppl 1, 2010, pp. S1-S9.

Pietra, Giuseppe G. et al., "Pathologic assessment of vasculopathies in pulmonary hypertension", Journal of the American College of Cardiology, vol. 43, No. 12 Suppl S, Jun. 16, 2004, pp. 25S-32S.

Provencher, Steeve et al., "Long-term outcome with first-line bosentan therapy in idiopathic pulmonary arterial hypertension", European Heart Journal, vol. 27, 2006, pp. 589-595.

Robbins, Ivan M. et al., "Association of the Metabolic Syndrome With Pulmonary Venous Hypertension", CHEST, vol. 136, No. 1, Jul. 2009, pp. 31-36.

Tanabe, Yasuhiko et al., "Significance of End-Tidal PCO2 Response to Exercise and Its Relation to Functional Capacity in Patients With Chronic Heart Failure", CHEST, vol. 119, No. 3, Mar. 2001, pp. 811-817.

Wilson, Robert F. et al., "Pulmonary Artery Diastolic and Wedge Pressure Relationships in Critically Ill and Injured Patients", Arch Surg, vol. 123, Aug. 1988, pp. 933-936.

Yasunobu, Yuji et al., "End-tidal PCO2 abnormality and exercise limitation in patients with primary pulmonary hypertension", Chest, vol. 127, 2005, pp. 1637-1646.

"Portable Bedside Capnograph / Pulse Oximeter Service Manual", NELLCOR OxiMax NPB-75, 65 pages.

09821158.4, European Application Serial No. 09821158.4, Extended European Search Report mailed Feb. 1, 2013, Anna R. Hemnes, et al, 9 pages.

Amis, Jr., Md, E. S. et al., "American College of Radiology White Paper on Radiation Dose in Medicine", Journal of the American College of Radiology, vol. 4, No. 5, 2007, pp. 272-284.

Anderson, MD, David R. et al., "Use of Spiral Computed Tomography Contrast Angiography and Ultrasonography to Exclude the Diagnosis of Pulmonary Embolism in the Emergency Department", The Journal of Emergency Medicine, vol. 29, No. 4, 2005, pp. 399-404.

Brenner, David J. et al., "Computed Tomography—An Increasing Source of Radiation Exposure", The New England Journal of Medicine Review Article, vol. 357;22, 2007, pp. 2277-2284.

Coche, MD, PHD, Emmanuel et al., "Pulmonary Embolism: Radiation Dose with Multi-Detector Row CT and Digital Angiography for Diagnosis1", Radiology, vol. 240, No. 3, Sep. 2006, pp. 690-697.

Demonaco, MD, Nicholas A. et al., "Pulmonary Embolism Incidence Is Increasing with Use of Spiral Computed Tomography", NIH Public Access American Journal of Medicine, Jul. 16, 2009, pp. 611-617.

Di Nisio, M. et al., "Diagnostic accuracy of D-dimer test for exclusion of venous thromboembolism: a systematic review", Journal of Thrombosis and Haemostasis, vol. 5, 2007, pp. 296-304.

Kline, MD, Jeffrey A. et al., "Diagnostic Accuracy of a Bedside D-dimer Assay and Alveolar Dead-Space Measurement for Rapid Exclusion of Pulmonary Embolism: A Multicenter Study", available at: http://jama.ama-assn.org/cgi/content/full/285/6/761, JAMA, vol. 285, No. 6, 2001, pp. 761-768.

Kline, MD, Jeffrey A. et al., "Use of the Alveolar Dead Space Fraction (Vd/Vt) and Plasma D-dimers to Exclude Acute Pulmonary Embolism in Ambulatory Patients", Academic Emergency Medicine, vol. 4, No. 9, Sep. 1997, pp. 856-863.

Lehman, MD, Christopher M. et al., "Analytic Validation and Clinical Evaluation of the STA LIATEST Immunoturbidimetric D-Dimer Assay for the Diagnosis of Disseminated Intravascular Coagulation", Coagulation and Transfusion Medicine / D-Dimer for the Diagnosis of DIC American Society for Clinical Pathology, vol. 122, 2004, pp. 178-184.

Miniati, Massimo et al., "Simple and Accurate Prediction of the Clinical Probability of Pulmonary Embolism", Am. J. Respir. Crit. Care Med., vol. 178, 2008, pp. 290-294.

PCT/US2009/060597, International Application Serial No. PCT/US2009/060597, International Preliminary Report on Patentability issued on Apr. 19, 2011, 5 pages.

PCT/US2009/060597, International Application Serial No. PCT/US2009/060597, International Search Report and Written Opinion mailed on Jan. 21, 2010, 6 pages.

(56) References Cited

OTHER PUBLICATIONS

PCT/US2012/033827, International Application Serial No. PCT/US2012/033827, International Search Report and Written Opinion mailed Nov. 30, 2012, 7 pages.
Perrier, MD, Arnaud et al., "Multidetector-Row Computed Tomography in Suspected Pulmonary Embolism", The New England Journal of Medicine, vol. 352;17, 2005, pp. 1760-1768.
Robin, MD, Eugene D. et al., "A physiologic Approach to the Diagnosis of Acute Pulmonary Embolism", The New England Journal of Medicine, Mar. 19, 1959, pp. 586-591.
Rodger, MD, MSC, Marc A. et al., "The Bedside Investigation of Pulmonary Embolism Diagnosis Study I A Double-blind Randomized Controlled Trial Comparing Combinations of 3 Bedside Tests vs Ventilation-Perfusion Scan for the Initial Investigation of Suspected Pulmonary Embolism", Arch Intern. Med., vol. 166, 2006, pp. 181-187.
Saltzman, MD, Herbert A. et al., "Value of the Ventilation/Perfusion Scan in Acute Pulmonary Embolism / Results of the Prospective Investigation of Pulmonary Embolism Diagnosis (PIOPED)", JAMA, vol. 263, No. 20, May 23/30, 1990, pp. 2753-2759.
Siragusa MD, Sergio et al., "Hemostasis & Thrombosis A rapid D-dimer assay in patients presenting at an emergency room with suspected acute venous thrombosis: accuracy and relation to clinical variables", haematologica, vol. 86(8), 2001, pp. 856-861.
Soubani, et al., "Noninvasive Monitoring of Oxygen and Carbon Dioxide", American Journal of Emergency Medicine, Centrum Philadelphia, PA, US, vol. 19, No. 2, XP005744007, ISSN: 0735-6757, DOI: 10.1053/AJEM.2001.21353, Mar. 2001, pp. 141-146.
Stein, MD, Paul D. et al., "D-Dimer for the Exclusion of Acute Venous Thrombosis and Pulmonary Embolism", Annals of Internal Medicine, vol. 140, No. 8, 2004, pp. 589-602.
Stein, MD, Paul D. et al., "Diagnostic Pathways in Acute Pulmonary Embolism: Recommendations of the PIOPED II Investigators1", Radiology, vol. 242, No. 1, Jan. 2007, pp. 15-21.
Stein, MD, Paul D. et al., "Multidetector Computed Tomography for Acute Pulmonary Embolism", The New England Journal of Medicine, vol. 354, No. 22, 2006, pp. 2317-2327.
Strzelczyk, PHD, Jadwiga (Jodi) et al., "Facts and Controversies About Radiation Exposure, Part 1: Controlling Unnecessary Radiation Exposures", J Am Coll Radiol, American College of Radiology, vol. 3, No. 12, 2006, pp. 924-931.
Strzelczyk, PHD, Jadwiga (Jodi) et al., "Facts and Controversies About Radiation Exposure, Part 2: Low-Level Exposures and Cancer Risk", J Am Coll Radiol, American College of Radiology, vol. 4, No. 1, 2007, pp. 32-39.
Tapson, MD, Victor F., "Acute Pulmonary Embolism", The New England Journal of Medicine, vol. 358;10, 2008, pp. 1037-1052.
Van Belle, MD, Arne et al., "Effectiveness of Managing Suspected Pulmonary Embolism Using an Algorithm Combining Clinical Probability, D-dimer Testing, and Computed Tomography", JAMA, vol. 295, No. 2, Jan. 11, 2006, pp. 172-179.
Verschuren, Franck et al., "Volumetric Capnography as a Screening Test for Pulmonary Embolism in the Emergency Department", CHEST—Official publication of the American College of Chest Physicians Chest, vol. 125, 2004, pp. 841-850.
Wells, MD, MSC, Philip S. et al., "Excluding Pulmonary Embolism at the Bedside without Diagnostic Imaging: Management of Patients with Suspected Pulmonary Embolism Presenting to the Emergency Department by Using a Simple Clinical Model and D-Dimer", Emergency Diagnosis of Pulmonary Embolism 2001 American College of Physicians-American Society of Internal Medicine, Annals of Internal Medicine, vol. 135, No. 2, 2001, pp. 98-107.
Yap, Kenneth S. et al., "A prospective reassessment of the utility of the Wells score in identifying pulmonary embolism", Medical Journal of Australia, vol. 187, No. 6, Sep. 17, 2007, pp. 333-336.

\* cited by examiner

1300

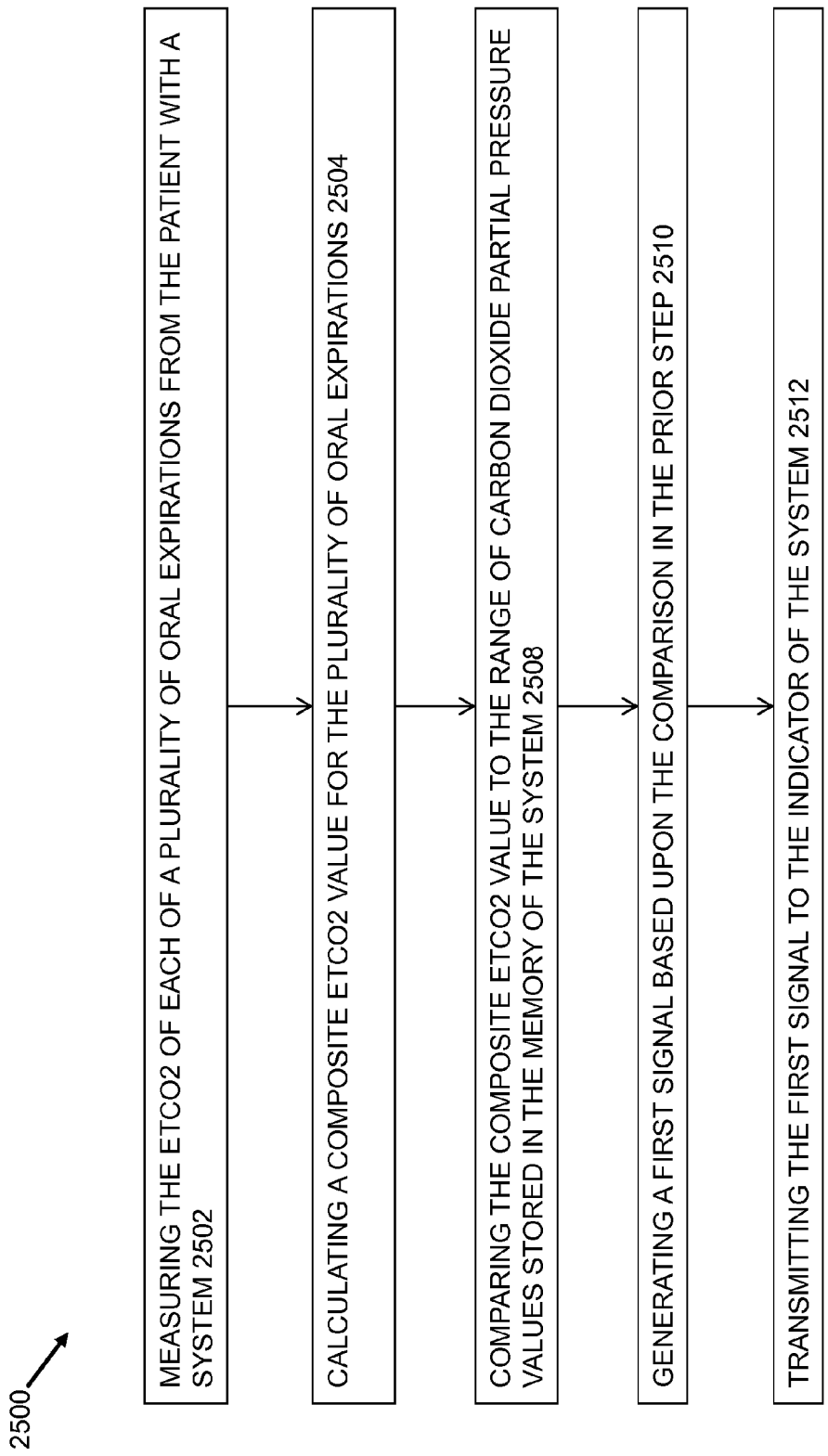

ORAL END TIDAL CARBON DIOXIDE PROBE FOR DIAGNOSING PULMONARY ARTERIAL HYPERTENSION

CROSS-REFERENCE TO RELATED APPLICATIONS

This application claims priority to U.S. patent application Ser. No. 61/476,133, filed Apr. 15, 2011, the entire disclosure of which is herein incorporated by reference.

This application is a continuation-in-part of the following U.S. patent applications, each of which is incorporated by reference in its entirety: U.S. patent application Ser. No. 12/578,841, filed Oct. 14, 2009, which claims the benefit of U.S. patent application Ser. No. 61/106,066, filed Oct. 16, 2008, the entire disclosure of which is herein incorporated by reference.

BACKGROUND

Field:

The present invention relates to an oral end tidal carbon dioxide probe.

Description of the Related Art:

Pulmonary embolism (PE) remains a diagnostic challenge and many studies are performed with a low yield at substantial financial cost and potential risk from radiation. End tidal carbon dioxide ($EtCO_2$) is a surrogate for pulmonary vascular obstruction and subsequent dead space ventilation. Using $EtCO_2$ as an initial screening test in patients being evaluated for PE would potentially spare many unnecessary, low-yield diagnostic studies and their associated risk and financial burden.

Pulmonary embolism (PE) is a common concern in the evaluation of diverse clinical presentations including chest pain, dyspnea and hypoxemia. Extensive diagnostic evaluation, including contrast enhanced helical computed tomography (CT), is frequently undertaken, despite a relatively low incidence of disease [2]. In addition to the cost of these studies, the risks of contrast and radiation exposure add to the burden of evaluation [3, 4]. Throughout this Specification, the numeral(s) inside of brackets refers to a literature citation. The list of literature cited appears at the end of the Detailed Description.

Diagnostic algorithms to simplify testing procedures in PE diagnosis have been explored, most combining D-dimer testing and CT angiography [5, 6]. D-dimer testing requires venipuncture and time for test performance. [1, 5] CT angiography use in PE diagnosis has increased markedly [2]. As a low percentage of CT angiograms demonstrate PE [2, 7, 8], concern has been raised of the contrast and radiation risk [4, 9]. Clinical prediction rules, including the Wells score, have also been proposed [6, 10] which have the advantage of instantaneous results, avoidance of invasive procedures, and low risk and cost.

With rising numbers of patients being evaluated for PH and the substantial cost, time, and potential risk in evaluation of pulmonary vascular disease [48], there is an interest in developing new, non-invasive diagnostic techniques to identify patients at low risk for PAH. Currently, final confirmation of diagnosis of PAH requires RHC, in part, to rule out PVH. While there are clinical and echocardiographic features that may make PVH more likely [31, 43], these indicators are often not adequately compelling to dissuade clinicians from pursuing RHC in patients with elevated right ventricular systolic pressure on echocardiography or evidence of cor pulmonale. Alternatively, clinicians may treat presumptive PAH with expensive and potentially harmful medications based on clinical and echocardiographic findings. Although cardiopulmonary exercise testing reveals differences in exhaled CO2 and ventilatory efficiency between patients with PAH and PVH [34, 38], this test is not available at the bedside, the required expertise is not found at some institutions, and has limitations in non-ambulatory patients.

Distinguishing pulmonary arterial hypertension (PAH) from other forms of pulmonary hypertension (PH) such as pulmonary venous hypertension (PVH) can be difficult at the bedside, even with use of echocardiography or other non-invasive techniques. While recent reports have suggested a potential role for analysis of "notch" pattern in right ventricular outflow tract Doppler flow velocity, right heart catheterization (RHC) with provocative procedures is usually required for accurate distinction of PAH from PVH associated with non-systolic heart failure [28-31]. This distinction is crucial as therapies for these two conditions and prognoses are different. Moreover, determining response to therapy in PAH is challenging with many well-described limitations of standard non-invasive six minute walk test (6MWT) [30, 32], and logistic challenges and expense with frequent RHC. Thus, there is a need for efficient, non-invasive testing of PE and distinguishing PAH from PVH and determining response to therapy in PAH is needed. A non-invasive, bedside test with good negative predictive value for PAH is a much needed diagnostic tool.

SUMMARY

The D-dimer test has been studied extensively in the exclusion of PE and its value in exclusion of low risk patients for further diagnostic evaluation is well established [1]. Despite a high negative predictive value in low risk patients [19], the D-dimer test has a highly variable sensitivity [20] and its interpretation can be confusing with multiple commercially available tests and cut-off values [19]. Most importantly, D-dimer testing requires venipuncture and time for transport, measurement and reporting which may increase total healthcare expenditure. A more rapidly available test would enhance speed of decision-making End tidal carbon dioxide ($EtCO_2$) level measurement is a physiological surrogate for diagnosing vascular obstruction resulting from PE. Pulmonary thromboembolism results in dead space ventilation and therefore prevents meaningful gas exchange in the subtended lung unit, yielding an alveolar $CO_2$ content as low as zero mmHg. As a result, carbon dioxide content measured at end expiration, which represents admixture of all alveolar gas, drops in proportion to dead space ventilation. While there are many potential etiologies of increased dead space ventilation including advanced chronic obstructive pulmonary disease, these diseases are usually easily identified. Increased dead space ventilation is not associated with common clinical conditions that can present similarly to pulmonary embolism e.g. unstable angina, gastroesophageal reflux. Dead space measurement and arterial-alveolar carbon dioxide tension gradient have been studied in the evaluation of PE [11-14], but the utility of end tidal $CO_2$ measurement alone in diagnosis of pulmonary embolism is not known. $EtCO_2$ is safe, non-invasive, inexpensive, and rapidly done at the bedside, whereas dead space measurement requires collection of exhaled gas and alveolar-arterial gradient requires arterial blood gas sampling.

In an aspect of the invention, a system and method of evaluating pulmonary embolism in a subject may include measuring carbon dioxide content at end expiration to obtain the end tidal partial pressure of exhaled carbon dioxide in the subject, wherein the measurement is made orally, obtaining a clinical approximation of dead space ventilation based on the measurement, and excluding pulmonary embolism when the end tidal partial pressure of exhaled carbon dioxide reaches a threshold. In the method and system, the threshold is at least 36 mm Hg. The method and system may further include applying a clinical prediction rule. The rule may include calculating a Wells score, and pulmonary embolism may be excluded when the Wells score is at least four. In the method and system, the subject may be a pediatric subject. In the method and system, the subject may be sedated. In the method and system, the subject may be intubated.

In an aspect of the invention, an oral capnometer may include an oral gas capture member, for collecting expired gases from the mouth, and a carbon dioxide measuring device attached to the oral gas capture member for determining levels of expired carbon dioxide from the mouth of a subject. In the method and system, the subject may be a pediatric subject. In the method and system, the subject may be sedated. In the method and system, the subject may be intubated. In the method and system, carbon dioxide levels may be measured continuously. In the method and system, the expired carbon dioxide may be end tidal carbon dioxide. In the method and system, the oral capnometer may be a portable capnometer. Further, the capnometer may include an indicator that may be able to indicate the presence of diseases. Such an indicator may be a visual indicator, audio indicator, audio-visual indicator, a binary indicator, and the like. In embodiments, the indicator may be indicative of a particular diagnosis, such as PAH or PE.

In an aspect of the invention, a method of measuring end tidal carbon dioxide in a subject may include collecting expired gases from the mouth through an oral gas capture member adapted to be disposed on the sampling input of a carbon dioxide measuring device and a carbon dioxide measuring device attached to the oral gas capture member for determining levels of expired carbon dioxide from the mouth of the subject. In another aspect of the invention, a method of measuring end tidal carbon dioxide in a subject may include a carbon dioxide measuring device that directly collects expired gases from the mouth of the subject by means of an integral gas capture chamber. In the method and system, the subject may be a pediatric subject. In the method and system, the subject may be sedated. In the method and system, the subject may be intubated. In the method and system, the subject may be awake. In the method and system, the subject may be spontaneously breathing. In the method and system, carbon dioxide levels may be measured continuously. In the method and system, the expired carbon dioxide may be end tidal carbon dioxide.

In an aspect of the invention, a system and method may comprise an oral gas capture member, for collecting expired gases from the mouth of a subject; a gas sensor for identifying and measuring at least one exhaled gas; and a housing for housing the gas sensor, wherein the housing is integral with the oral gas capture member. In the system and method, the exhaled gas may be at least one of carbon dioxide, carbon monoxide, nitrogen, oxygen, and ketone. In the system and method, the subject may be at least one of awake, spontaneously breathing, pediatric, sedated, intubated, sleeping, and the like. In the system and method, gas levels may be measured continuously. In the system and method, the expired carbon dioxide may be end tidal carbon dioxide. In the system and method, the gas sensor may also the measure pH of an exhaled gas.

In an aspect of the invention, an oral capnometer for measuring end-tidal carbon dioxide is provided. The capnometer may include an airway adapter, a filter, a sensor, and a display unit. The airway adapter may be configured to allow passage of respiratory gases. In an aspect, the airway adapter may include a first port and a second port. The first port of the airway adapter may be dedicated for carbon dioxide intake. The second port of the airway adapter may be dedicated for pressure and temperature measurements. Further, the filter provided in the capnometer may be connected to the airway adapter and may be able to separate water from carbon dioxide. In addition, the sensor may enable detection of respiratory parameters of the respiratory gases. In an aspect, the sensor may be a galvanic fuel cell. In another aspect, the sensor may be integrated in a mechanical pod. Further, the display unit may be configured to the sensor for displaying waveforms thereon. In an aspect, the display unit may be able to display the waveforms through an interface. In another aspect, the display unit may be an LCD display, an LED display, and the like.

In the method and the system, the oral capnometer may include an optical bench to enhance stable, accurate measurements from a small sample. The oral capnometer may also include a pulse oximeter that may be able to monitor oxygen saturation of a patient's blood. In the method and the system, the oral capnometer may include a printer that may be able to print measurement data. Further, the oral capnometer may also include an interface option that may enable direct printing with an external printer. In the method and the system, the oral capnometer may further include an interface option that may function as a computer connection port. In embodiments, the oral capnometer may include an interface option for connection with a pulse oximeter. In the method and the system, the oral capnometer may be used with an R-series defibrillator. In the method and the system, the oral capnometer may also include an alarm. The alarm may be preset for certain levels of end-tidal carbon dioxide. In the method and the system, the oral capnometer may also include a turbine flow meter. The turbine flow meter may be a digital turbine flow meter. Further, the turbine flow meter may be bidirectional. In an aspect, the turbine flow meter may require an antibacterial filter. In the method and the system, the oral capnometer may include a differential pressure transducer. The differential pressure transducer may not require an antibacterial filter. In the method and the system, the oral capnometer may further includesoftware for data management and reporting.

In embodiments, the oral capnometer may be a portable capnometer. In the method and the system, the oral capnometer may be a handheld capnometer. In the method and the system, the oral capnometer may be light in weight. Further, the oral capnometer may be operated by means of one of a battery and AC means.

In an aspect of the invention, an oral capnometer for measuring end tidal carbon dioxide is provided. The oral capnometer may also include an oral gas capture member, an end tidal carbon dioxide detection device, and an indicator 1008. The oral gas capture member may collect expired gases from the mouth. The end tidal carbon dioxide detection device may be attached to the oral gas capture member and may determine levels of the end tidal carbon dioxide at end expiration from the mouth of a subject. The end tidal carbon dioxide detection device may include a pressure sensor to determine pressure of the end tidal carbon dioxide.

The indicator 1008 may be activated when the level of the end tidal carbon dioxide falls below a pre-determined threshold value.

In an aspect of the invention, the oral gas capture member may collect expired gases from the mouth at pre-determined regular intervals. In an aspect of the invention, the pressure sensor of the end tidal carbon dioxide detection device is a differential pressure sensor. In an aspect of the invention, the end tidal carbon dioxide detection device may be configured to detect pulmonary arterial hypertension.

In an aspect of the invention, the end tidal carbon dioxide detection device may be configured to detect a level of pulmonary arterial hypertension such that the level of pulmonary arterial hypertension may be monitored over a time interval.

These and other systems, methods, objects, features, and advantages of the present invention will be apparent to those skilled in the art from the following detailed description of the preferred embodiment and the drawings. All documents mentioned herein are hereby incorporated in their entirety by reference.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The invention and the following detailed description of certain embodiments thereof may be understood by reference to the following figures:

FIG. 25 depicts a flow chart of a method related to diagnosing pulmonary arterial hypertension.

DETAILED DESCRIPTION

End tidal CO2 detection may be used to differentiate pulmonary arterial hypertension (PAH) patients from those with normal pulmonary blood vessels or pulmonary venous hypertension patients as well as to diagnose pulmonary embolism (PE) in patients. A carbon dioxide measurement and analysis device enables emergent evaluation of PE patients and outpatient management of PAH patients. For example, the rise in end tidal carbon dioxide can be used to detect successful therapy in patients with established PAH, which has not been demonstrated previously.

Figure 6:
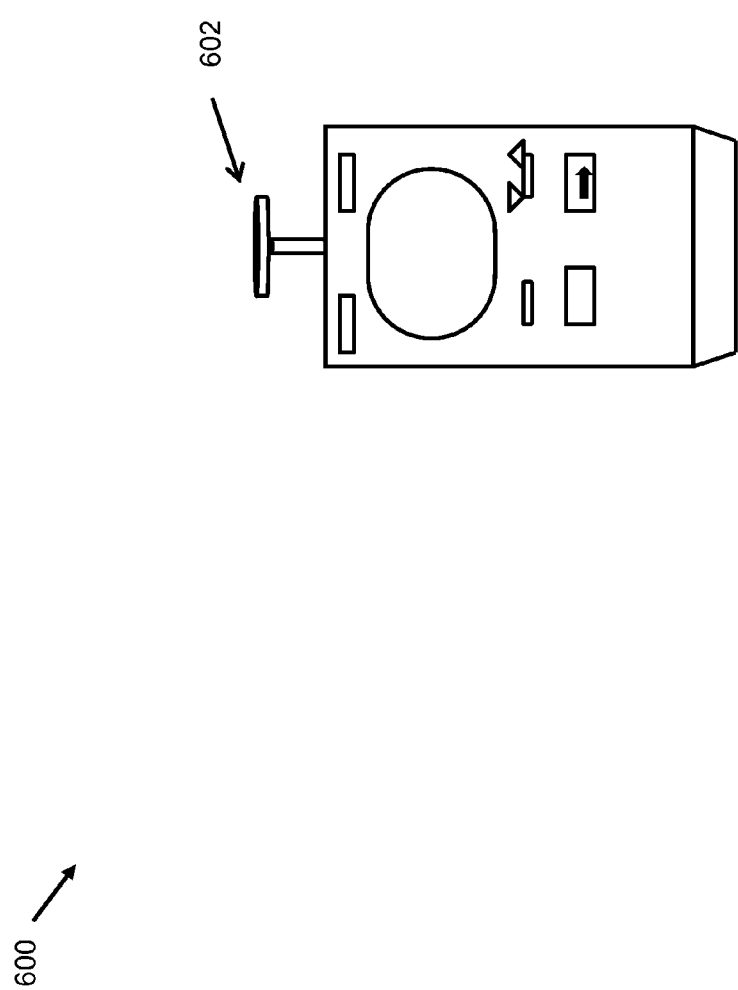
FIG. 6 depicts the invention in which the gas capture chamber forms an integral part of the capnometer.

The present disclosure also concerns an oral capnometer 102 for measuring end tidal carbon dioxide content as it is exhaled from the mouth. Sampling orally exhaled gases may comprise using a capnometer or capnograph with an adaptor on the sampling input to enable oral sampling, as in FIG. 1, an integral oral gas capture member as in FIG. 6, or a detachably engaged oral gas capture member as in FIG. 7. For example, the oral capnometer 102 may be attached to plastic tubing with an adapter that is placed in the mouth. The adapter may be sized to sample gases exhaled from the oral cavity. In other embodiments, the present invention may be an integral oral gas capture member 602 in which the capturing space is connected integrally to the capnometer. In still other embodiments, the oral sampling space may be interchangeably attached to the capnometer to facilitate measurements of exhaled gasses from subjects of various sizes or states of health. Sampling gases from the mouth instead of the nose enables more accurate measurement of exhaled gases as nasal sampling may cause hyperventilation. For example and without limitation, oral sampling of exhaled gases may enable more accurate measurements of end tidal carbon dioxide ($EtCO_2$), and therefore, more accurate estimation of dead space ventilation.

By measuring $EtCO_2$2 in patients undergoing evaluation for PE without controlling clinical care or management, predictions may be made regarding PE status. For example, $EtCO_2$ may be reduced in patients with PE and a normal $EtCO_2$ measurement may have a high negative predictive value to exclude PE.

Figure 7:
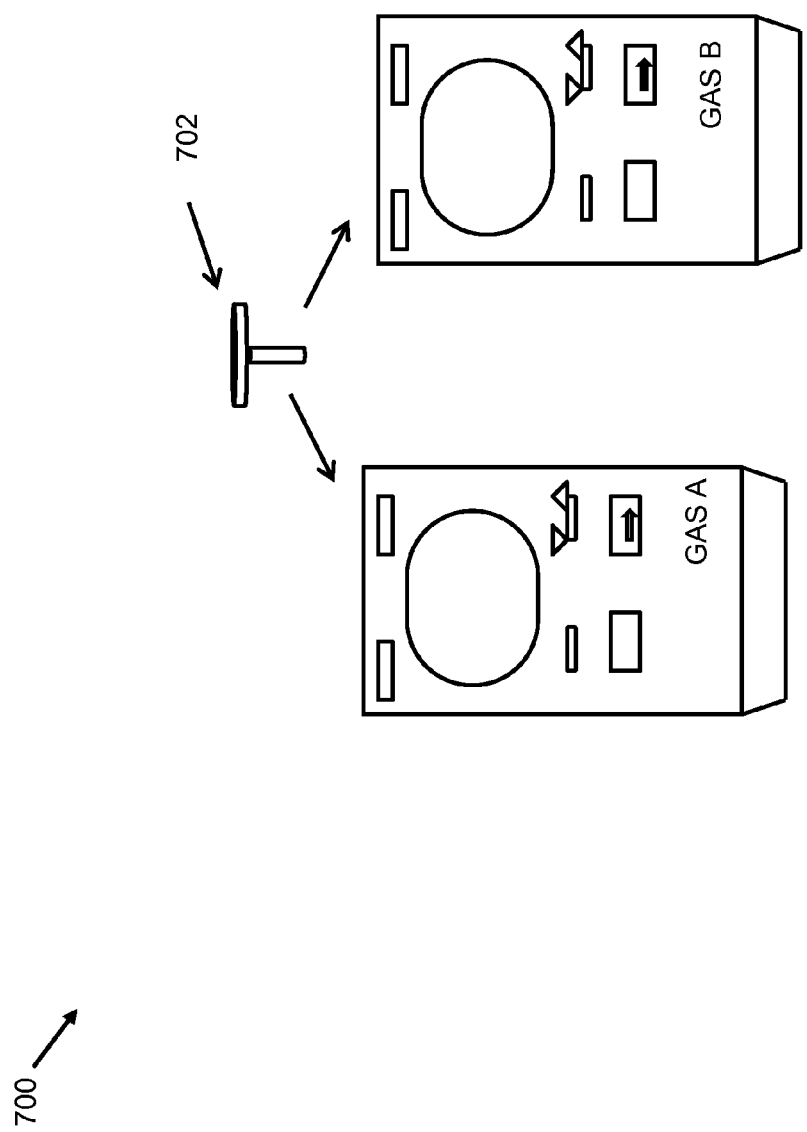
FIG. 7 depicts the invention in which the gas capture chamber is detachably attached to the capnometer, such that other measuring devices may be attached to the gas capture chamber.

The oral capnometer 102 may also be useful for measuring exhaled oxygen levels, such as for estimating cardiac output or other metabolic equivalents. The oral capnometer 102 may also be useful for measuring exhaled carbon monoxide levels, such as in the detection of ongoing cigarette smoking, carbon monoxide poisoning, and the like. The oral capnometer 102 may also be useful for measuring exhaled residual compounds left in the lungs to aid in the diagnosis of some cancers. The oral capnometer 102 may also be useful for measuring exhaled ketones, such as in the diagnosis of ketoacidosis. The oral capnometer 102 may also be useful for measuring the pH of exhaled gas for diagnosis of metabolic acidosis in lactic acidosis or diabetic ketoacidosis. The oral capnometer 102 may also be useful for measuring exhaled nitrogen. The oral capnometer 102 may comprise a gas sensor that is capable of measuring many different gases and pH levels. Alternatively, each gas may be sensed by an individual gas sensor housed separately. Thus, the oral gas capture member 702 may be detachably associated, as shown in FIG. 7 for two devices measuring "Gas A" and "Gas B", with the oral capnometer 102 such that if measurement of a gas with another gas sensing device is required, the oral gas capture member may be attached to and used with the device. In an embodiment, multiple sizes and shapes of oral gas capture members, suitable for subjects of different ages, sizes and physical conditions, may be detachably attached to the oral capnometer 102.

Figure 3:
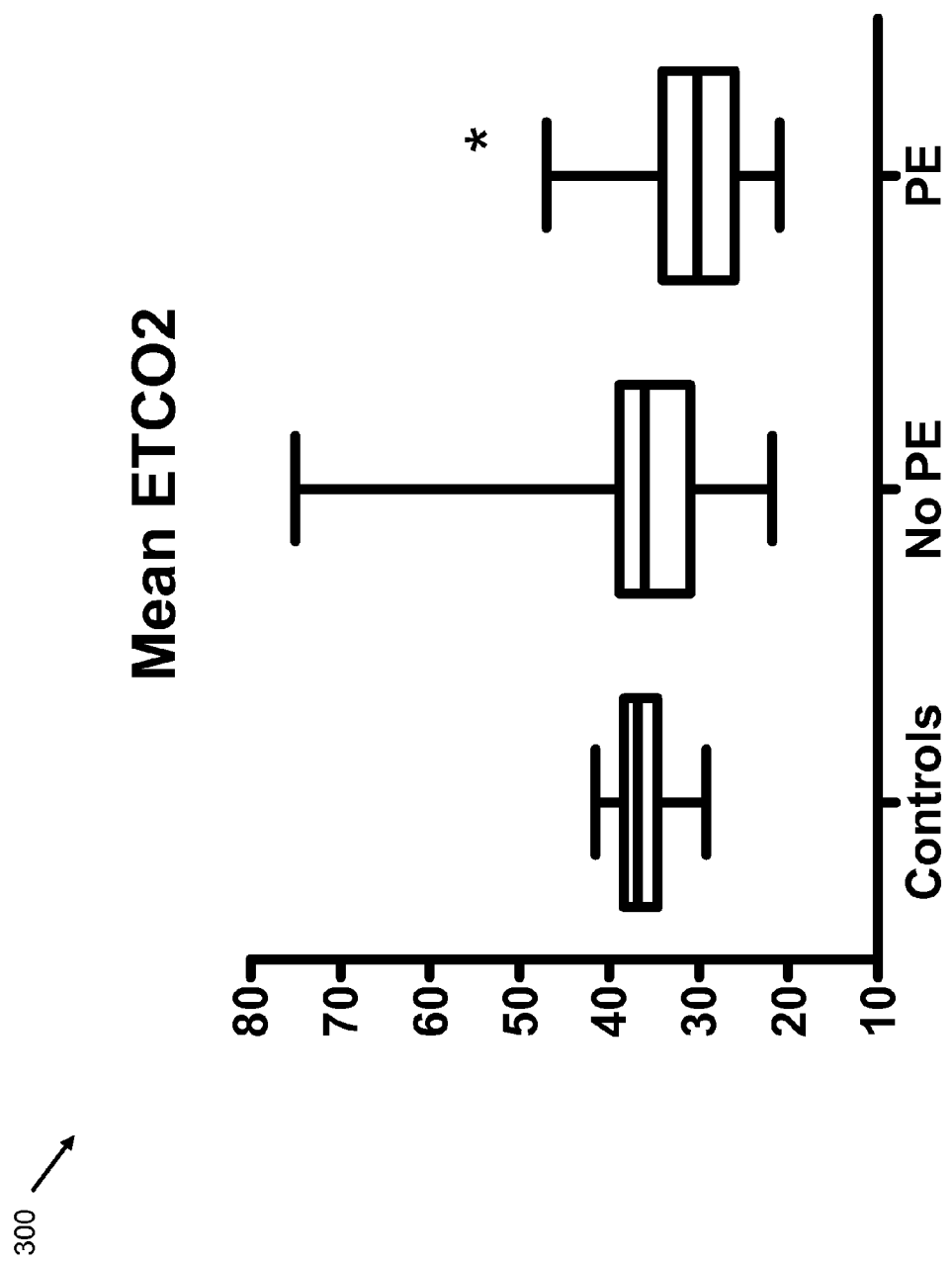
FIG. 3 depicts end tidal carbon dioxide in normal volunteers, patients without pulmonary embolism, and patients with pulmonary embolism.

In order to demonstrate the usefulness of accurate end tidal carbon dioxide sampling, the oral capnometer 102 of the invention was used in defining the optimal end tidal carbon dioxide ($EtCO_2$) level in the exclusion of pulmonary embolism (PE) in patients undergoing evaluation of possible thromboembolism. The oral capnometer 102 of the invention was used in a study involving 298 patients conducted over 6 months at a single academic center. $EtCO_2$ was measured within 24 hours of contrast enhanced helical CT, lower extremity duplex or ventilation/perfusion scan. Performance characteristics were measured by comparing test results with clinical diagnosis of PE. The results of the study using the oral capnometer 102 were that PE was diagnosed in 39 patients (13%). FIG. 3 depicts mean end tidal carbon dioxide±SD in healthy volunteers, patients without pulmonary embolism (no pulmonary embolism) and patients with pulmonary embolism (pulmonary embolism). The data had a p<0.05 vs. healthy volunteers and no pulmonary embolism group. The mean $EtCO_2$ in the healthy volunteers was not different from $EtCO_2$ in the enrolled patients without PE (36.3±2.8, SD mmHg vs. 35.5±6.8 mmHg), as shown in FIG. 3. $EtCO_2$ in the patients with PE was 30.5±5.5 mmHg (p<0.001 versus no PE group). $EtCO_2$ of ≥36 mmHg had optimal sensitivity and specificity (87.2 and 53.0% respectively) with a negative predictive value of 96.6% (92.3-98.5 95% CI). This increased to 97.6% (93.2-99.2 95% CI) when combined with a Wells score <4. $EtCO_2$ of ≥36 mmHg may reliably exclude PE. Accuracy is augmented by combination with a Wells score. $EtCO_2$ may be prospectively compared to D-dimer in accuracy and simplicity to exclude PE.

All patients ≥18 years of age who were seen in the Emergency Department or inpatient wards at an academic university hospital over the six month period were screened electronically for a computer order for contrasted chest helical CT, ventilation-perfusion lung scan, pulmonary angiogram or lower extremity Duplex evaluation. Patients meeting screening criteria were approached for consent to undergo $EtCO_2$ within 24 hours of study order placement. Exclusion criteria were inability to consent, pregnancy, known hypercarbic respiratory failure, mechanical ventilation, face mask oxygen or more than 5 L/minute nasal cannula oxygen or known neuromuscular disease. Patients who presented for evaluation more than once could be enrolled multiple times (n=5, two studies each).

Figure 1:
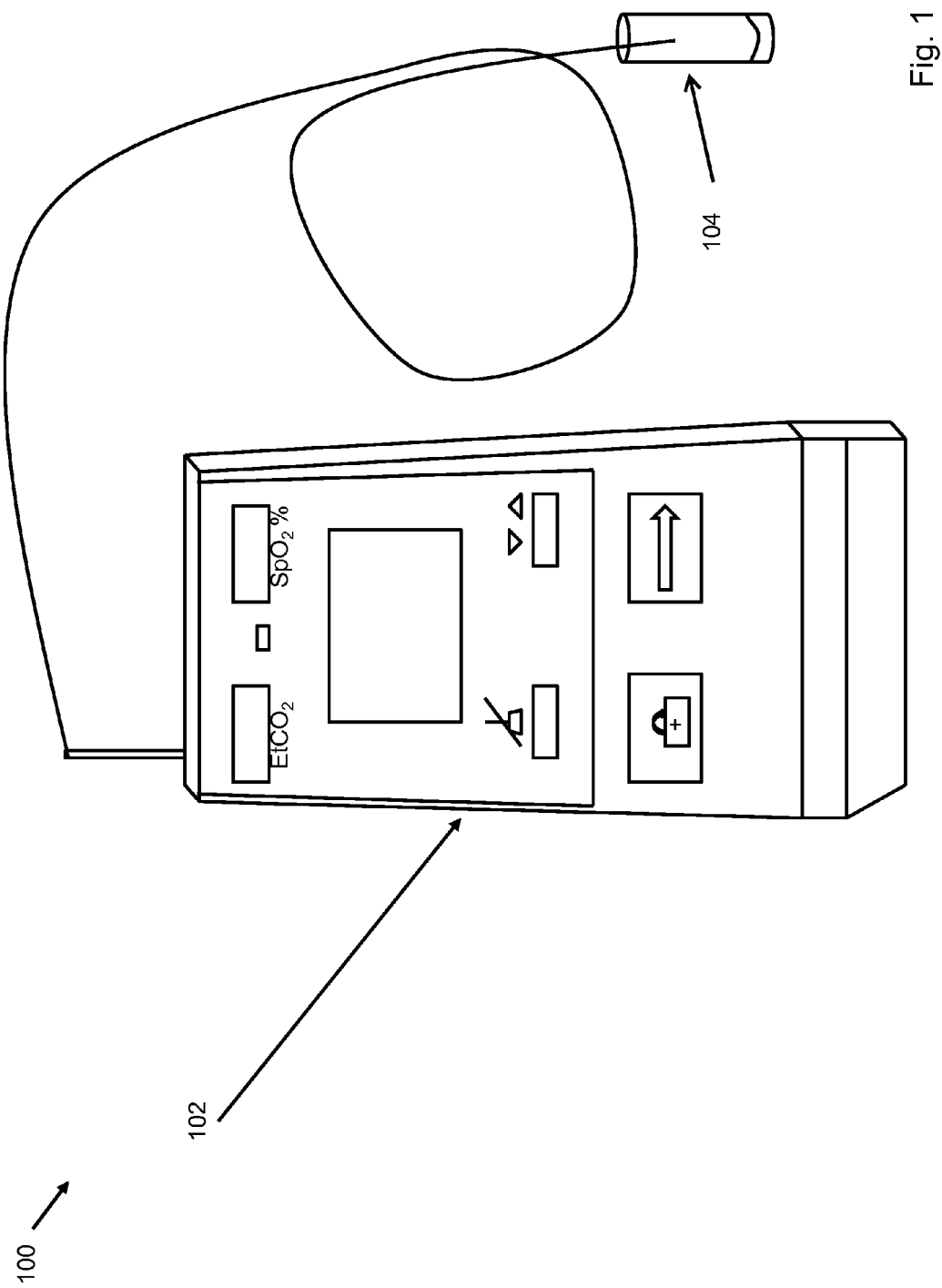
FIG. 1 depicts an image of the modified capnometer of the invention.

$EtCO_2$ was measured by a trained single tester blinded to diagnosis using the oral capnometer 102 of the invention [15]. The device may be calibrated to ±2 mmHg up to 38 mmHg and ±0.08% for every 1 mmHg over 40 mmHg. The oral capnometer 102 is different from capnometers used to measure exhalation from the nostrils in that the uptake cannula is inserted into a plastic tube that, when placed in the mouth, may enable patients to tidally breathe while $CO_2$ is measured, as shown in FIG. 1. $CO_2$ Patients were instructed to breathe normally and were tested for five breaths in either a supine or seated position. Nostrils were not clipped shut. $EtCO_2$ for each breath and respiratory rate were measured. The oral capnometer 102 of the invention was validated every two weeks at two levels of $CO_2$ using an exercise machine calibrated to zero and 5.6% $CO_2$. Patient charts were analyzed for demographic data including comorbid conditions and thromboembolic risks, self-reported race/ethnicity (categorized into Hispanic, African-American, Caucasian, or other) results of serum chemistries, blood counts, ventilation/perfusion lung scan, CT (such as Brilliance CT 64 Channel, Phillips, Amsterdam, The Netherlands), pulmonary angiography, and venous duplex exams. Wells score [6] was assigned by a single physician, blinded from final diagnosis, from data obtained at the time that diagnostic tests were ordered. Plasma D-dimer testing (STA LIATEST, Diagnostica Stago, Parsippany, N.J.[16]) was performed at the discretion of the treating physician. Patients with D-dimer testing alone for PE were not included in this study because of the risk of false positive D-dimer tests.

Pulmonary embolism was defined by a published consensus criteria [1] including positive contrast-enhanced CT, intermediate or high probability ventilation perfusion lung scan (as described in PIOPED I [17]) combined with high pretest probability, or positive lower extremity duplex examination with a high clinical suspicion for PE.

To ensure accuracy and reproducibility, and to standardize the modified sensing device, and discover stability of $EtCO_2$ measurements over time in healthy individuals, $EtCO_2$ was measured for five breaths in 24 healthy volunteers (mean age 40.0 (12.0), 10/24 male) on three different days. Additionally, $EtCO_2$ was measured with different $FiO_2$ delivered by nasal cannula up to 51 pm and found no difference (data not shown).

Based on the study center's experience and previous work [8, 18], a 15% positive rate of diagnostic tests for patients undergoing PE evaluation was assumed. Given this diagnostic rate and a standard deviation of 2.8 mmHg in $EtCO_2$ measurements in normal volunteers, a sample size calculation determined that 300 patients would be required to detect a difference in $EtCO_2$ of 1.3 mmHg between groups with 80% power at an alpha level of 0.05. This sample size would allow detection of a difference of 9% in sensitivity compared to the Wells score <4[6]. Continuous variables are reported as mean (standard deviation) and analyzed using Student's t-test or Wilcoxon Rank Sum testing. Categorical variables are reported as percentages and were analyzed using Fisher's Exact test. Receiver Operating Characteristic (ROC) curves with area under the curve (AUC) were used for determining the optimal $EtCO_2$ to discriminate between patients with and without PE. All p-values are two-tailed and values ≤0.05 were considered significant. Data analyses were done using both R version 2.7.1 and SPSS (Version 15.0; Chicago, Ill., USA).

Figure 2:
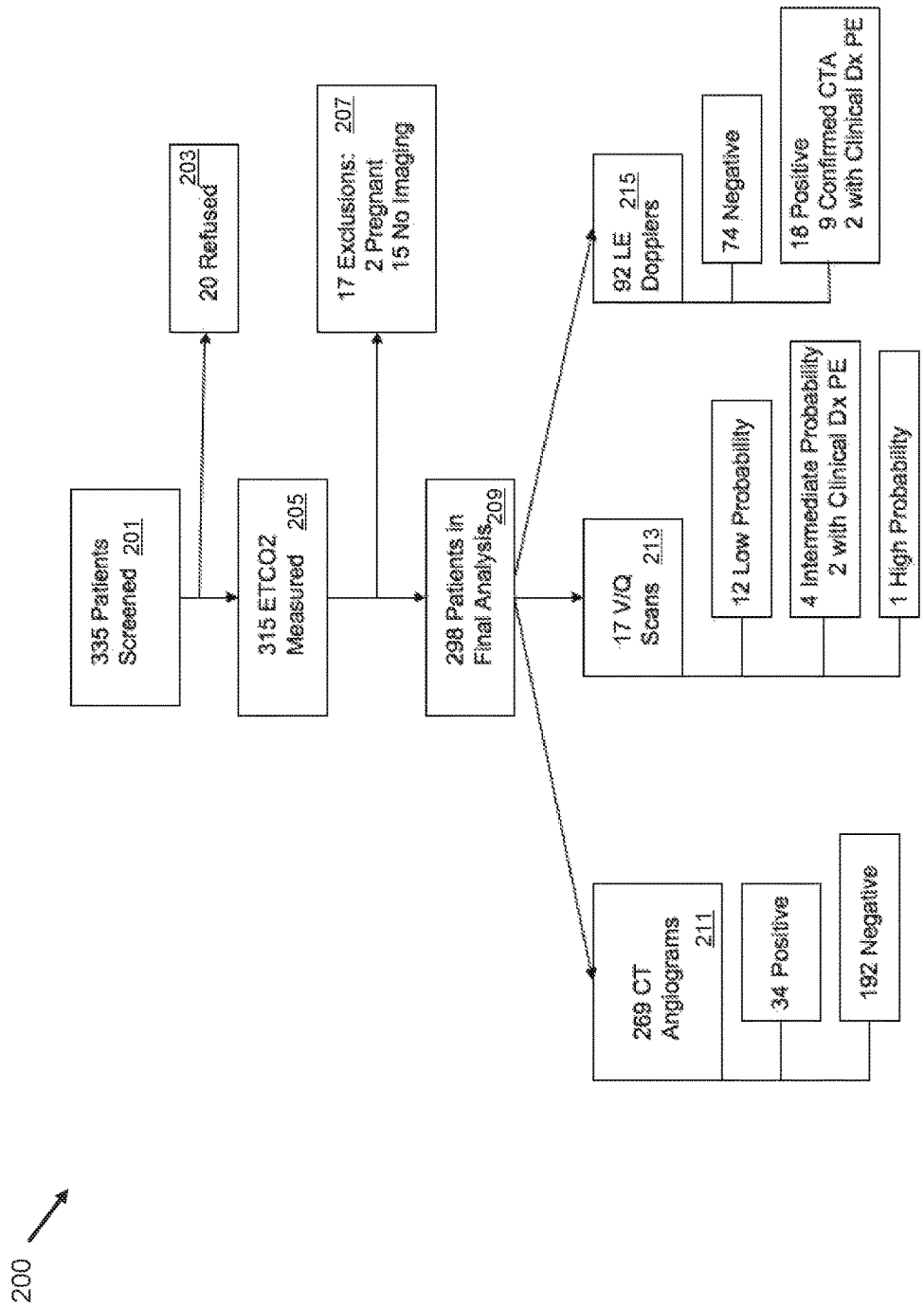
FIG. 2 depicts a study flow diagram.

Referring to FIG. 2, a study flow diagram is shown. The study flow diagram shows that, at step 201, a total of 335 patients were screened and approached for entry into the trial. At step 203, twenty patients did not consent. At step 205, of the 315 patients in whom $EtCO_2$ was measured, 17 patients were excluded at step 207 after enrollment (two were found to be pregnant and 15 did not have any imaging studies, as in FIG. 2. At step 209, of the remaining 298 patients included in the final analysis, 269 patients had CT angiograms at step 211, 17 patients had V/Q scans at step 213, and 92 had lower extremity (LE) doppler examination at step 215. 39 patients were diagnosed with pulmonary embolism (34 positive helical CT, three intermediate or high probability ventilation perfusion scans with high clinical suspicion, two positive lower extremity duplex examinations with high clinical suspicion). Five patients were enrolled twice. One hundred eighty patients were enrolled from the Emergency Department with 21 PEs and 118 were inpatients with 18 PEs.

Demographic characteristics of the group as a whole and the sub-categories of those with and without PE are shown in Table 1 (Data are presented as mean±SD unless otherwise stated, n=298 unless otherwise stated, p values are for No PE vs. PE groups.)

TABLE 1

Demographics

| | All (n = 298) | No PE (n = 259) | PE (n = 39) | p Value |
|---|---|---|---|---|
| Age (yrs) | 52.1 ± 17.2 | 51.0 ± 17.1 | 59.5 ± 16.05 | 0.004 |
| Gender (% female) | 53 | 54 | 46 | 0.36 |
| Race (%, n = 294) | | | | |
| White | 72 | 72 | 77 | |
| African-American | 25 | 25 | 23 | |
| Other | 3 | 3 | 0 | |
| Smoking (%, n = 290) | | | | |
| Never | 53 | 53 | 54 | 0.39 |
| Current | 32 | 33 | 24 | |
| Past | 15 | 14 | 22 | |
| Comorbidities (%) | | | | |
| None | 33 | 33 | 31 | 0.17 |
| Diabetes | 3 | 2 | 10 | |
| Hypertension | 25 | 25 | 23 | |
| Diabetes + hypertension | 13 | 14 | 8 | |
| Cancer | 13 | 12 | 15 | |
| Chronic lung disease | 6 | 7 | 3 | |
| Other | 7 | 7 | 10 | |
| PE Risk Factors (%) | | | | |
| None | 62 | 68 | 18 | <0.001 |
| Post-operative | 4 | 4 | 5 | |
| Cancer | 13 | 12 | 18 | |
| Post-partum | 1 | 1 | 0 | |
| Immobilized | 3 | 2 | 8 | |
| Previous DVT/PE | 8 | 7 | 13 | |
| Multiple | 8 | 4 | 33 | |
| Other | 1 | 0 | 5 | |

There was no difference in age, gender, ethnicity, smoking status or presence or absence of medical comorbidities in the two groups. The group with PE was significantly enriched for the presence of one or more risk factors for venous thromboembolic disease than the no PE group (p<0.001). The group without PE had a range of diagnoses from no cause identified (n=44, 17%), pulmonary disease such as COPD, asthma or lung cancer (n=84, 32%), and cardiac disease (n=48, 19%) to musculoskeletal disease, neuromuscular disease, and deep venous thrombosis without PE which made up the remainder.

Patients with PE were less likely than those without PE to undergo chest CT imaging for chest pain alone (p=0.01 PE vs. No PE groups, Table 2), however there were no significant differences in the other indications for chest imaging between the two groups. (Data are presented as mean±SD unless otherwise stated, n=298 unless otherwise stated, p values are for No PE vs. PE groups.) The mean Wells score was 4.3±2.5 in the group with PE and 1.7±1.9 (p<0.001) in the no PE group. Five of 39 patients with PE had a Wells score ≤2.0. Fourteen percent of CTs in the emergency department were positive for PE and 17% of CTs ordered as an inpatient were positive for PE. 97/298 patients had serum D-dimer measured, of these 47 were negative (0 PEs) and 48 positive (4 PEs).

TABLE 2

Presenting Features of Study Enrollees

| | All (n = 298) | No PE (n = 259) | PE (n = 39) | p Value |
|---|---|---|---|---|
| Indication for PE evaluation (%) | | | | |
| Chest pain | 35 | 37 | 23 | 0.006 |
| Hypoxemia | 1 | 0 | 5 | |
| Dyspnea | 25 | 24 | 31 | |
| Hemoptysis | 0 | 0 | 3 | |
| Fever | 6 | 6 | 5 | |
| Chest pain and dyspnea | 9 | 8 | 15 | |
| Limb swelling/pain | 4 | 4 | 3 | |
| Miscellaneous | 20 | 21 | 15 | |
| Wells score | 2.0 ± 2.1 | 1.7 ± 1.9 | 4.3 ± 2.5 | <0.001 |
| Heart rate (bpm) | 86.2 ± 17.1 | 86.0 ± 17.1 | 87.8 ± 15.0 | 0.42 |
| Systolic blood pressure (mmHg) | 125.3 ± 20.7 | 126.3 ± 21.0 | 118.7 ± 17.0 | 0.02 |
| Diastolic blood pressure (mmHg) | 72.2 ± 14.5 | 72.5 ± 15.0 | 70.4 ± 10.5 | 0.37 |
| Respiratory rate (bpm) | 17.2 ± 6.2 | 17.0 ± 6.3 | 18.6 ± 5.6 | 0.09 |
| Oxygen saturation (%) | 96.6 ± 2.6 | 96.6 ± 2.6 | 96.4 ± 2.3 | 0.39 |
| Supplemental oxygen (%) | 26 | 24 | 44 | 0.01 |

In normal volunteers, mean $EtCO_2$ was 36.3±2.8 mmHg (95% CI 35.1-37.4, Table 3). Data are presented as mean±SD, n=24. There were no significant differences among the five measured breaths each day or among the mean $EtCO_2$s in an individual over the three separate days. Age and gender did not affect $EtCO_2$.

TABLE 3

$EtCO_2$ in normal individuals over 5 separate days

| Age (yrs) | 40.0 ± 12.0 | |
|---|---|---|
| Female no. | 14 | |
| Smoking no. | | |
| Never | 20 | |
| Past | 4 | |
| Current | 0 | |
| $EtCO_2$ by breath (Day 1) (mmHg) | | p = 0.21 |
| Breath 1 | 36.7 ± 3.0 | |
| Breath 2 | 36.3 ± 2.9 | |
| Breath 3 | 36.7 ± 3.0 | |
| Breath 4 | 37.1 ± 3.5 | |
| Breath 5 | 37.3 ± 3.6 | |
| $EtCO_2$ by day (mmHg) | | p = 0.25 |
| Day 1 | 36.6 ± 3.0 | |

TABLE 3-continued

EtCO$_2$ in normal individuals over 5 separate days

| Day 2 | 36.6 ± 3.8 |
|---|---|
| Day 3 | 35.6 ± 3.6 |
| Overall mean EtCO$_2$ (mmHg) | 36.4 ± 2.8 |

There was no significant difference in EtCO$_2$ between normal controls and the no PE group (36.3±2.8 mmHg vs. 35.5±6.8 mmHg respectively, p=0.56, FIG. 3). The group with PE had a significantly lower EtCO$_2$ (30.5±5.5 mmHg, vs. healthy volunteers p<0.001), which was also significant compared with the no PE group (P<0.001). Mean EtCO$_2$ was not different in the two D-dimer groups (35.3±5.9 mmHg D-dimer positive vs. 36.1±5.2 in D-dimer negative groups, p=0.35). There were no adverse events related to EtCO$_2$ measurement.

Figure 4:
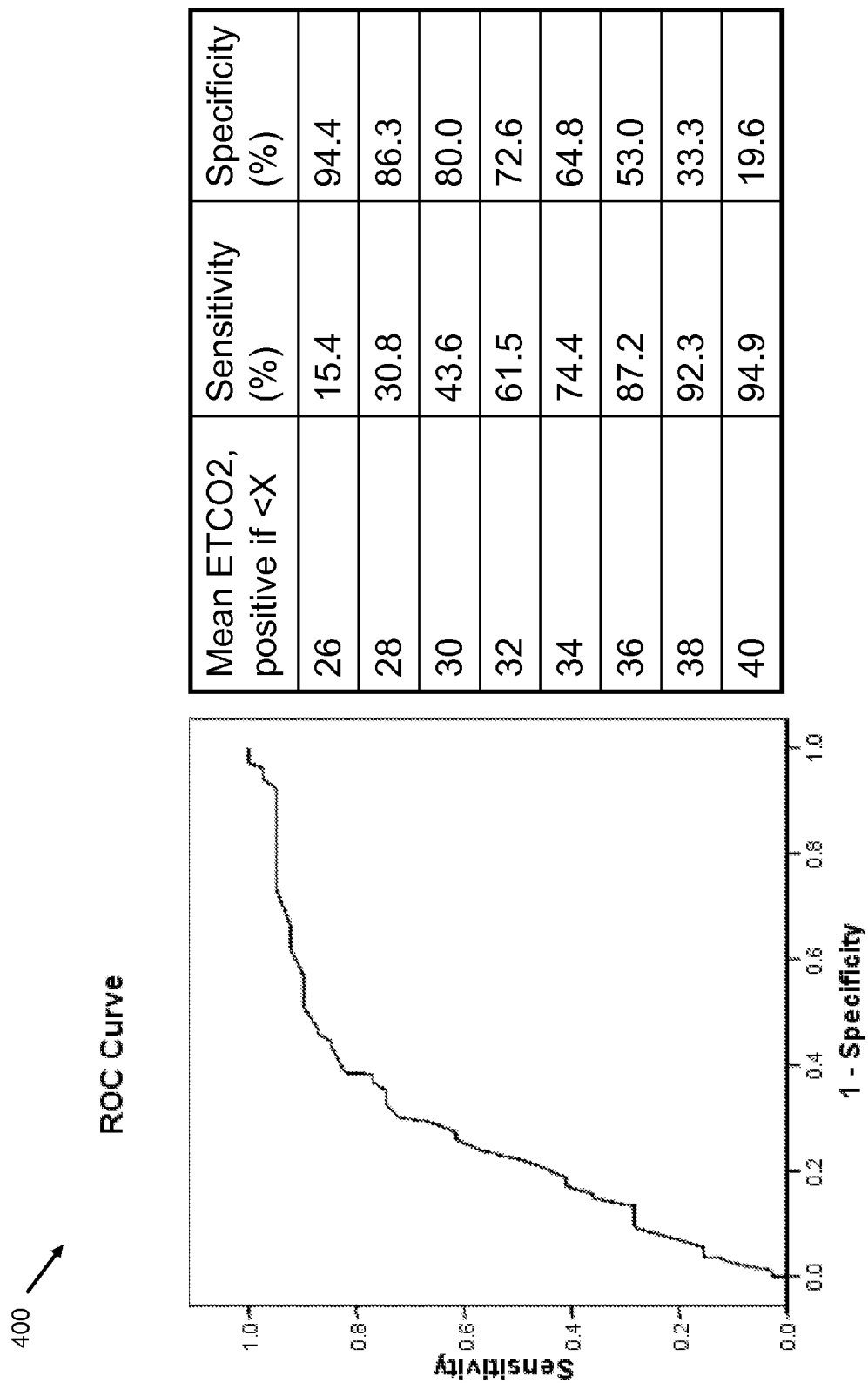
FIG. 4 depicts end tidal carbon dioxide performance characteristics and pulmonary embolism diagnosis.

A receiver operator characteristics (ROC) curve demonstrating the ability of EtCO$_2$ to discriminate between patients with and without PE and the corresponding sensitivities and specificities to a given EtCo$_2$ measurement are shown in FIG. 4 (AUC=0.739). In order to avoid the most unnecessary procedures in the diagnosis of PE while maintaining optimal sensitivity for diagnosis, a cut off of 36 mmHg was chosen for further analysis of the characteristics of this test. At this cut off, the negative predictive value was 96.6% (95% CI 92.3-98.5, Table 4).

TABLE 4

Test performance characteristics

| | Sensitivity (%, 95% CI) | Specificity (%, 95% CI) | Positive Predictive Value (%, 95% CI) | Negative Predictive Value (%, 95% CI) |
|---|---|---|---|---|
| EtCO$_2$ <36 All Comers | 87.2 (73.3-94.4) | 53.0 (47.0-58.8) | 21.1 (15.5-28.1) | 96.6 (92.3-98.5) |
| EtCO$_2$ <36, excluding >44 | 91.9 (78.7-97.2) | 49.0 (42.8-55.2) | 21.1 (15.5-28.1) | 97.6 (93.2-99.2) |
| Wells Score ≥4 | 61.5 (45.9-75.1) | 83.3 (78.4-87.3) | 34.8 (24.6-46.6) | 93.8 (89.9-96.2) |
| EtCO$_2$ <36 All Comers + Wells Score ≥4 | 92.3 (79.7-97.3) | 45.2 (39.4-51.1) | 19.6 (14.5-25.9) | 97.6 (93.2-99.2) |

When patients with EtCO$_2$≥36 mmHg but <44 mmHg (2.78 SD above normal) were analyzed, there was an increase in negative predictive value to 97.6% (95% CI 93.2-99.2). A negative predictive value for Wells score<4 of 93.8% (95% CI 89.9-96.2) was found in this population. In combining the Wells score<4 with the EtCO$_2$>36 mmHg without restriction on maximum EtCO$_2$, the negative predictive value again rose to 97.6% (95% CI 93.2-99.2).

In this study, it was shown that a safe, simple, inexpensive, bedside test for EtCO$_2$ has a high negative predictive value in excluding PE and that the EtCO$_2$ measured with the oral capnometer 102 of the invention in combination with the Wells Score improves negative predictive value to a very high level of accuracy.

Dead space fraction (Vd/Vt), measured by comparing total exhaled partial pressure CO$_2$ (pCO$_2$) with arterial partial pressure CO$_2$ (paCO$_2$), has previously been shown to be abnormal in pulmonary embolism and Vd/Vt in combination with D-dimer testing is effective at ruling out PE [11-13, 21]. However, the requirement of specialized equipment and an arterial puncture limit its widespread adaptation. EtCO$_2$ measured only with the oral capnometer 102 is a surrogate for dead space measurement.

Various cut off levels of EtCO$_2$ were examined to determine optimal sensitivity and specificity of this test. Using a cut off of ≥36 mmHg, a negative predictive value of 96.6% was achieved, which is similar to that reported with d-dimer testing [19]. There was a small improvement after excluding patients with an EtCO$_2$ significantly outside of the range of normal, but might confuse clinical decision-making without a concomitantly large improvement in test characteristics. The addition of the Wells score<4 to the EtCO$_2$ measurement similarly numerically improved the testing characteristics without adding further confusion about patient exclusions. It was found that at the lower levels of EtCO$_2$, there was a substantial increase in specificity for PE. This improved specificity at lower EtCO$_2$ levels is in marked contrast with D-dimer, with results that are either positive or negative.

In the study group, 166 subjects had an EtCO$_2$>36 mmHg and would not have undergone further testing if that were used as the sole criterion for ruling out PE. Of these 166 subjects, 20 had a Wells score of 4.0 or higher. Thus, in the study, 146/298 (49%) of subjects would have been spared further evaluation for PE using these criteria. Three of 39 PEs would be missed in the study using these criteria. All three of these patients were discovered to have hypoventilation after further evaluation during the hospitalization (morbid obesity, chronic narcotic use and interstitial lung disease).

The importance of sparing these diagnostic procedures is not trivial. In the cohort, 226 patients (76%) underwent diagnostic CT scanning The long-term risks of exposure to radiation from chest CT scanning are a concern [4, 9, 22, 23]. The typical contrast-enhanced chest CT for pulmonary embolism evaluation delivers approximately 20 mSv of radiation [4, 24]. This dose from a single CT approaches the 40 mSv widely thought of as a dangerous limit from historical data [4, 22, 24]. In this study alone, five people were enrolled twice in the six-month study. While there is debate about the "safe limit" of radiation exposure, the American College of Radiology has called for controlling unnecessary radiation exposure [23]. The monetary savings from preventing unnecessary CT studies is also potentially substantial. For example, at a cost per study of $1739 [25], patients in the study underwent a total of 226 contrast enhanced helical CTs, 120 of which could potentially be spared saving $208,680. The study included both inpatients and patients in the Emergency Department to capture the complete population perceived to be at risk for PE. Because patients who underwent only D-dimer testing were not included, the pre-test probability for PE in the cohort may have been increased. Despite this potential bias, EtCO$_2$ was similar in the normal controls and the group without PE, suggesting that physiologically the group without PE was similar to normals. Too few patients had PEs in the group with D-dimer data to allow a meaningful direct comparison with EtCO$_2$. While the CT positivity rate for PE was lower than some prior published reports [7, 8, 26], it is similar to other publications in the literature and may represent local practice patterns [21, 27]. The EtCO$_2$ would likely be abnormal in conditions affecting metabolic activity or carbon dioxide excretion such as pregnancy, end-stage chronic obstructive lung disease or advanced neuromuscular disease; therefore patients known to have these conditions from participation were excluded, totaling fewer than 10 patients. Thyroid disease at its extremes may affect EtCO$_2$ results, but this is often not known at initial evaluation, thus these patients were not excluded. EtCO$_2$ cannot distinguish between type of pulmonary arterial obstruction such as acute PE, chronic thromboembolic disease or tumor emboli. No CT angiograms showed changes typical for chronic thromboembolic pulmonary hypertension.

Thus, a cheap, simple, readily available, non-invasive test of EtCO$_2$ combined with a bedside prediction tool may be useful to exclude pulmonary embolism in patients without pregnancy or advanced lung or neuromuscular disease.

Accurate measurement of orally exhaled gases may be useful additionally in a pediatric population, with patients under sedation, with patients who have been intubated, to measure expired gases continuously, and the like.

Figure 5:
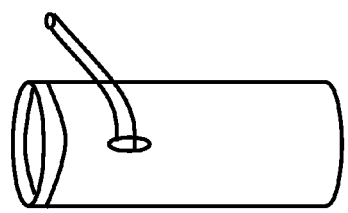
FIG. 5 depicts the oral gas capture member of the invention.

The oral capnometer 102 of the invention may be constructed by adapting the sampling input of a capnometer, as shown in FIG. 1, with an oral adaptor. For example, the oral adaptor may be a hollow-bodied oral gas capture member that sits in a subject's mouth, having formed in the member an aperture through which a subject may exhale gases and an aperture for placement of a sampling tube of the capnometer that positions the sampling tube within the capture member and allows exhaled gases to enter the sampling tube. In embodiments, the adaptor may be of any shape and may bear any markings For example, as in FIG. 5, the sampling tube may be placed through a hole in the sidewall of a hollow tube. In an embodiment, the tube may have dimensions of 1.5 cm diameter×5 cm length. The sampling tube may be formed from flexible, plastic tubing. The oral gas capture member may be formed from any suitable material, such as plastic, metal, glass, or the like. In an embodiment, the oral gas capture member may be disposable.

The oral capnometer 102 may be used to construct a capnograph by measuring carbon dioxide levels over time.

The oral capnometer 102 may be useful in measuring carbon dioxide levels in order to estimate cardiac output and metabolism; diagnose hypoventilation, bronchitis, emphysema, asthma, congenital heart disease, hypothermia, diabetes, circulatory shock; and obtain information about the effectiveness of CPR and the return of spontaneous circulation (ROSC), CO$_2$ production, pulmonary (lung) perfusion, alveolar ventilation, respiratory patterns, and elimination of CO$_2$ from the anesthesia breathing circuit and ventilator.

In an embodiment, evaluating pulmonary embolism in a subject may include measuring end tidal partial pressure of exhaled carbon dioxide in the subject, wherein the measurement is made orally, obtaining a clinical approximation of dead space ventilation based on the measurement, and excluding pulmonary embolism when the end tidal partial pressure of exhaled carbon dioxide reaches a threshold. The threshold may be at least 36 mm Hg. The evaluation may further include applying a clinical prediction rule. The rule may include calculating a Wells score, and pulmonary embolism may be excluded when the Wells score is at least four. The subject may be a pediatric subject, sedated, intubated, and the like.

In an embodiment, an oral capnometer 102 may include an oral gas capture member 104, 602, 702, for collecting expired gases from the mouth, and a carbon dioxide measuring device attached to the oral gas capture member 104, 602, 702 for determining levels of expired carbon dioxide from the mouth of a subject. The subject may be a pediatric subject, sedated, intubated, and the like. Carbon dioxide levels may be measured continuously. The expired carbon dioxide may be end tidal carbon dioxide.

In an embodiment, a method of measuring end tidal carbon dioxide in a subject may include collecting expired gases from the mouth through an oral gas capture member 104, 702 adapted to be disposed on the sampling input of a carbon dioxide measuring device and determining levels of expired carbon dioxide in the expired gas. In another embodiment, a method of measuring end tidal carbon dioxide in a subject may include a carbon dioxide measuring device that directly collects expired gases from the mouth of the subject by means of an integral gas capture chamber 602. The subject may be a pediatric subject, sedated, intubated, awake, spontaneously breathing, and the like. Carbon dioxide levels may be measured continuously. The expired carbon dioxide may be end tidal carbon dioxide.

In an embodiment, an oral capnometer 102 may include an oral gas capture member 602 for collecting expired gases from the mouth of a subject; a gas sensor for identifying and measuring at least one exhaled gas; and a housing for housing the gas sensor, wherein the housing is integral with the oral gas capture member 602. The exhaled gas may be at least one of carbon dioxide, carbon monoxide, nitrogen, oxygen, and ketone. The subject may be at least one of awake, spontaneously breathing, pediatric, sedated, intubated, sleeping, and the like. Gas levels may be measured continuously. The expired carbon dioxide may be end tidal carbon dioxide. The gas sensor may also the measure pH of an exhaled gas.

Figure 8:
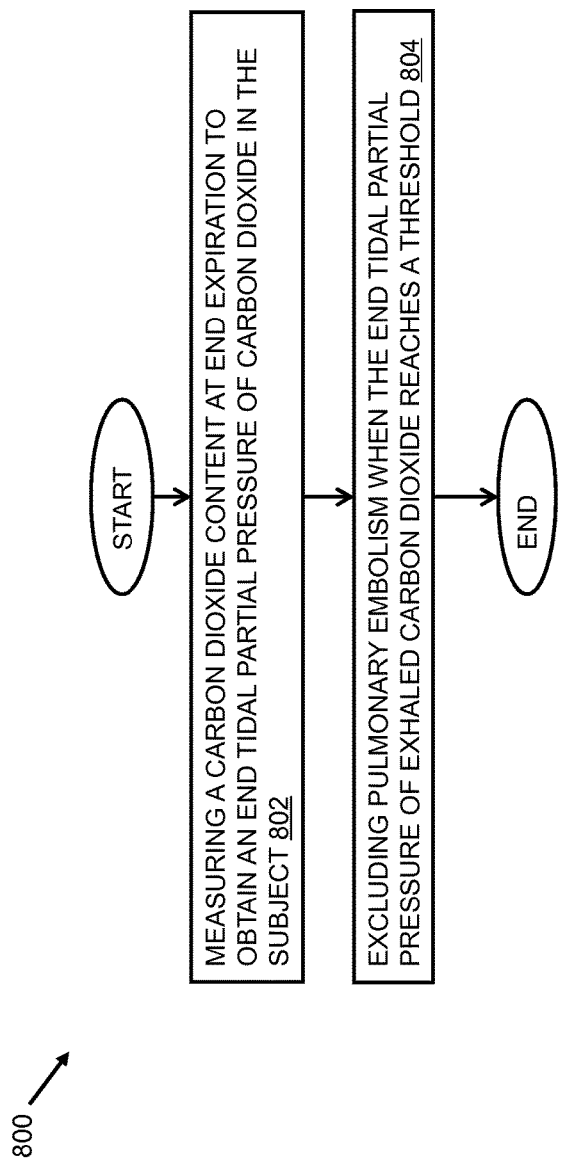
FIG. 8 depicts a flow chart of a method for excluding pulmonary embolism.

Referring to FIG. 8, a method of evaluating pulmonary embolism in a subject may include measuring a carbon dioxide content at end expiration to obtain an end tidal partial pressure of carbon dioxide in the subject 802 and excluding pulmonary embolism when the end tidal partial pressure of exhaled carbon dioxide reaches a threshold 804. The measurement may be made orally. A clinical approximation of dead space ventilation is based on the measurement. The threshold may be at least 36 mm Hg. The method of evaluating pulmonary embolism may further include applying a clinical prediction rule. The rule may include calculating a Wells score. Pulmonary embolism is excluded when the Wells score is at least four. The subject may be at least one of sedated, intubated, and pediatric.

Figure 9:
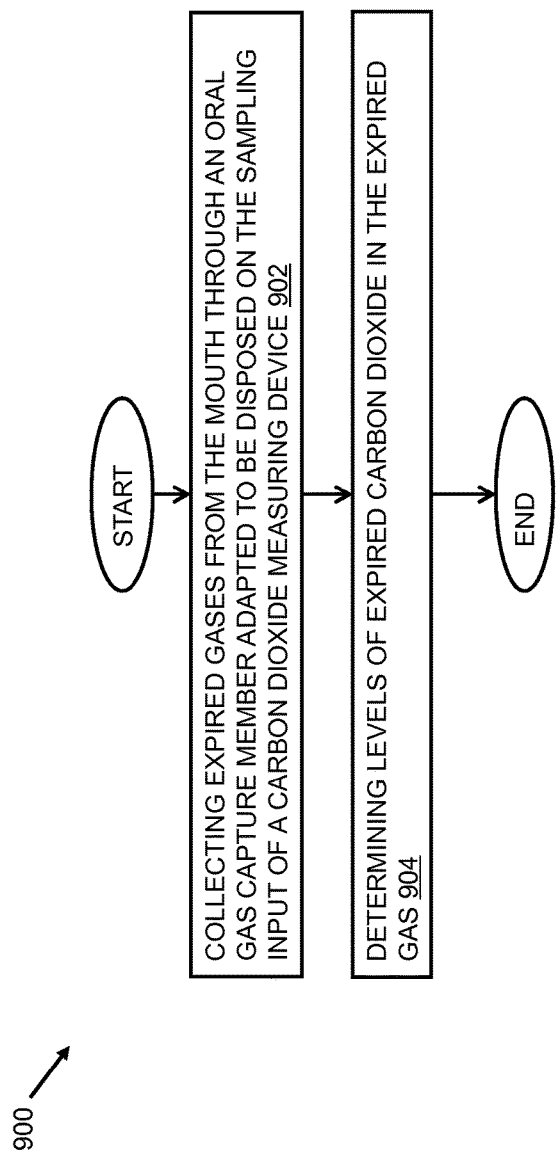
FIG. 9 depicts a flow chart of a method of measuring end tidal carbon dioxide in a subject.

Referring to FIG. 9, a method of measuring end tidal carbon dioxide in a subject may include collecting expired gases from the mouth through an oral gas capture member adapted to be disposed on the sampling input of a carbon dioxide measuring device 902 and determining levels of expired carbon dioxide in the expired gas 904. The subject is at least one of sedated, intubated, and pediatric. The carbon dioxide levels may be measured continuously. The expired carbon dioxide may be end tidal carbon dioxide.

Further, the capnometer may include an integrated sensor or sensor array that may be able to detect the presence of a disease. Integrated sensors enable the measurement and characterization of other respiratory gas components, some of which may be indicative of disease. For example, an integrated sensor may be able to detect elevated levels of acetone in the exhaled breath for a preliminary diagnosis of diabetes. In another example, a sensor for detecting nitric oxide may be able to detect the presence of asthma. In embodiments, the sensor may be a sensor operable to detect chemicals in exhaled breath, in the saliva, in the blood, on the skin, in the urine, and the like. In embodiments where the sensor is not for measuring exhaled breath components, the sensor may be integrated in a part of the capnometer readily accessible by a user for carrying out the measurement.

When the sensor detects a disease, an indicator 1008 may be activated. Such an indicator may be a visual indicator, audio indicator, audio-visual indicator, a binary indicator, and the like.

The capnometer may include an airway adapter, a filter, a sensor, and a display unit. The airway adapter may be configured to allow passage of respiratory gases. For example, a first port of the airway adapter may be dedicated for carbon dioxide intake, while a second port of the airway adapter may be dedicated for pressure and temperature measurements. Further, the filter provided in the capnometer may be connected to the airway adapter and may be able to separate water from carbon dioxide. In addition, the sensor may enable detection of respiratory parameters of the respiratory gases. In an aspect, the sensor may be a galvanic fuel cell. In another aspect, the sensor may be integrated in a mechanical pod.

The display unit may be configured to the sensor or sensor array for displaying waveforms thereon. In an aspect, the display unit may be able to display the waveforms through an interface. In another aspect, the display unit may be an LCD display, an LED display, and the like.

In an embodiment, the oral capnometer may include an optical bench to enhance stable, accurate measurements from a small sample. In an example, a low sample flow rate of 50 ml/min may allow monitoring a wide range of patients with the oral capnometer without compromising on the response time. The oral capnometer may be adapted to monitor EtCO2 for intubated or non-intubated neonatal through adult patients. In another embodiment, the oral capnometer may include a user interface that may be useful for displaying waveforms and trends. The waveforms and trends may include but are not limited to capnographic waveforms and trends, SpO2 graphical trends, and plethysmographic waveforms. Further, the user interface may be used for setting user-adjustable alarms. In an embodiment, the user interface may have menus in multiple languages so that the user may select a language of his/her choice. Further, the user interface may enable data output and printing, and the like.

In embodiments, the oral capnometer may include pulse oximetry technology. The oral capnometer may handle moisture with the help of an integrated water separation filter in each connector and a multi-port airway adapter design as well as no cross-sensitivity to other gases, such as anesthetic agents. The oral capnometer may warm-up quickly and require no routine calibration. The oral capnometer may further include a first port for $CO_2$ and a second port that may be used for invasive pressure or temperature. The oral capnometer may be embodied in a portable, handheld form factor that may weigh less than two pounds and may be operated by AC, battery, and the like.

In embodiments, CO2 detectors may be used to detect approximate ranges of EtCO2 in adult and infant intubated patients to assist in the verification of tube placement during endotracheal or nasotracheal intubation. The detectors may be attached to the endotracheal tube to provide breath by breath visual feedback on the levels of exhaled CO2. The visual feedback may include a color change method from purple to yellow. In an example, the purple color is indicative of 0.03% to 0.5% CO2 in the breath, the tan color is indicative of 0.5% to 2% CO2 in the breath and the yellow color is indicative of 2% to 5% CO2 in the breath.

In an embodiment, if the endotracheal tube is placed correctly the visual feedback may be alternate between purple and yellow colors. In embodiments, an adult detector may be used for patients weighing more than 15 kg. The adult detector may weigh less than 20 g, and may have an internal volume of 25 cc. Further, a pediatric care detector may be used for patients weighing from 1 to 15 kg. Such a detector may weigh 5 grams and may have an internal volume of 3 cc. The detectors (adult and pediatric) may have two connection ports. One connection port may be connected to the endotracheal tube and the other end may be connected to the resuscitation bag. Both the detectors are small and are meant for single usage and may be used for up to two hours.

In an embodiment, the oral capnometer may include an optical bench that may provide stability during cold temperatures making the oral capnometer good for use during patient transport. The oral capnometer may also be used for clinical settings where fast and easy $EtCO_2$ monitoring may be required. The oral capnometer may be equipped with fast, first breath $EtCO_2$ technology that may provide measurement data with the first breath. Further, the oral capnometer may be used for endotracheal tube placement verifications, waveform trend monitoring, detecting breathing irregularities, gauging the efficacy of CPR and procedural sedation monitoring. The oral capnometer's sidestream design may allow it to be used with both intubated and non-intubated neonatal through adult patients. The oral capnometer may provide $EtCO_2$, $FiCO_2$, respiratory rate and $CO_2$ waveform data using a simple serial protocol. The oral capnometer may use advanced algorithms that may adjust for $CO_2$ absorption, temperature, pressure, altitude, and respiration rate. In addition, the oral capnometer may require no interruption to compensate for drift. The oral capnometer may function quietly and may have dimensions of 60×96×25 mm. The oral capnometer may weigh 32 g with a 21 g pump plus tubing & water trap. Further, the oral capnometer may have a flow of 75 ml/min.

In embodiments, a cardiopulmonary testing system may be used in clinical settings for early detection of heart conditions and to manage heart failure disease. The system may include a device that may include a data analyzer, a disposable patient interface or mask, a pulse oximeter, a computer, and a printer. Further, the system may measure ventilatory gas parameters, VE/CO2 slope, and chronotropic indices while the patient may exercise for a certain period of time. In a test, four to five therapy settings of a patient are tested. At the end of the test, the cardiopulmonary testing system may use a computer algorithm to rank the physiological response to exercise at each setting. In an embodiment, the system may provide real time data interpretations. In an aspect of the present invention, the system may be used to quantify a patient's functional capacity, assess patient risk, and obtain a trend of the patient's response to therapy over time. The system may also be used to conduct different tests such as low-intensity graded protocol exercise test, a standard incremental protocol exercise test, and a steady state test. In addition, the cardiopulmonary testing system may measure cardiopulmonary gas exchange without any undue strain on the patient and may be used in clinical settings by any trained clinical employee.

In an embodiment, the device may perform cardiopulmonary exercise tests and displays results on a color LCD user interface with the option of printing the results. The device may also measure forced vital capacity, maximum voluntary ventilation, pre & post bronchial dilator response, and slow vital capacity (inspiratory & expiratory). The device may include a sensor that may be a galvanic fuel cell. Further, the device may use a dynamic mixing chamber. In an exemplary embodiment, the device may be used in clinical settings for all ages. Further, the device may have a flow range of 0.08-2.0 l/s. In an embodiment, the device may weigh 1.5 kg and may have 24×20×8 cm dimensions.

In an aspect, the device may be a hand held device designed for flexible spirometry screening for all age groups. The device may be used to perform tests easily and accurately wherever it is needed. The results of the tests conducted by the device may be viewed on a user interface. The user interface may be a black and white LCD display. In an embodiment, the results may also be printed by linking the device directly to an external printer or to a PC through a USB port. Further, the device may be a portable spirometer designed to measure ventilatory SpO2 and HR parameters. The device may also measure forced vital capacity, maximum voluntary ventilation, bronchial dilator test, the bronchial challenge test, and the like. In an embodiment, the device may be used in clinics by primary care practitioners, in mobile clinical settings, as a preventative measure, in sports medicine, and the like. The device may provide three USB interfacing options for direct printing with an external inkjet or laser printer (PCL compatible). The USB interfacing options may also be used as PC connection port, for connection with pulse oximeter for SpO2 monitoring, and the like.

Further, the device may be available in three different configurations. A first configuration may be a basic model of the device that may include a bidirectional digital turbine flow meter. The digital turbine flow meter may require use of antibacterial filters. In an embodiment, in a second configuration, the device may be available as a disposable device that may have a single use differential pressure transducer. The differential pressure transducer may be designed to avoid risk of cross contamination especially in hospital settings. Further, the differential pressure transducer may not require antibacterial filter. A third configuration of the device may include a turbine flow meter and a silicone face mask with head cap and SpO2 monitor. The SpO2 monitor may measure ventilatory parameters and oxygen saturation during a "six minute walking test".

In embodiments, the device may come with PC software that may be used for data management and reporting. The device may include an internal memory which may store up to 1000 tests/patients. In an exemplary embodiment, the device may be a hand held device with a compact size of 18×7.5×3 cms and may weigh less than 400 gram. The device may be embodied in a simple operating mode through a navigation tool similar to cellular phones. The device may also be equipped with a rechargeable battery that may last up to 6 hours.

In embodiments, the device may be embodied in a mechanical pod and may be used as a non-invasive device for intensive care monitoring of endotracheal EtCO2. Further, the sensor and the mechanical pod may integrate respiratory parameters, waveforms and flow loops with hemodynamic data on one display. The mechanical pod may include a housing. The housing may further include a flow sensor, a combined CO2/flow sensor, a CO2 sensor connector (20-pin); and a monitor connector (7-pin). The CO2/flow sensor may be encoded for automatic patient category identification. Further, the Sensor may be used for neonatal, pediatric and adult EtCO2 measurements. In an exemplary embodiment, the sensor may have the dimensions of 1.3×1.7×0.9 in. and may weigh 18 g. The parameters that may be measured are Carbon dioxide, inspired CO2, partial pressure arterial CO2, mixed expired CO2, end-tidal CO2, and at end-expiration (sidestream).

In embodiments, the device may be a portable bedside monitor that may be used in hospital areas where patients of all ages may be at risk for opioid-induced respiratory depression and arrest. The device may be used for all sedation procedures and patient controlled analgesia (PCA). Further, the device may includes superior algorithms that may reduce alarms, improve workflow and may provide clinical utility for improved patient safety. The device may offer both capnography and pulse oximetry in one monitor. Further, the device may work in a wide range of temperature environments and measure $CO_2$ in the presence of various gases. In an embodiment, the device may not need manual calibration, zeroing, water traps, flushing of monitor between uses, and the like.

In an exemplary embodiment, the device may have a flow rate of 50 ml/min which makes the device especially suitable for neonatal sampling. The device may provide an inclusive assessment of patient's ventilatory status. Further, the device may be a light-weight monitor which may have a battery life of up to 2 hours which makes it usable for transport. The monitor may be used for the verification of endotracheal tube or dislodgement of endotracheal tube during transport, for monitoring the effectiveness of chest compressions during CPR, useful in determining the ventilatory status of patients with asthma/COPD, and the like.The device may come with an optional choice of pulse oximetry. The device may include a large, color display with a fast, easy to use knob navigated flat menu structure. In an embodiment, date may be exported from the monitor through its USB port. As mentioned herein, the device may be used in all hospital areas and specifically in general patient care, procedural sedations, in critical care units, in post anesthesia care unit, and in emergency care.

In embodiments, a portable monitor may employ capnography technology to provide accurate, continuous monitoring on intubated and non-intubated patients. The monitor may be used for neonate to adult patients in hospital settings and emergency transport and other pre-hospital environments. Further, the monitor may be a light-weight monitor that may measure $EtCO_2$ without the need to calibrate for presence of other gases and may work in a wide range of temperature environments. The monitor may not need manual calibration, zeroing, water traps, flushing of monitor between uses, and the like. In addition, the monitor may have a flow rate of only 50 ml/min which makes the monitor suitable for neonatal sampling.

In embodiments, a monitor may have capnography and pulse oximetry in one convenient portable device. The monitor may provide accurate, continuous monitoring on intubated and non-intubated patients from neonate to adult in hospital and pre-hospital environments, including emergency transport. Further, the monitor may be a light-weight monitor that may measure $EtCO_2$ without the need to calibrate for presence of other gases and works in a wide range of temperature environments. The monitor may not need manual calibration, zeroing, water traps, flushing of monitor between uses, and the like. Also, the monitor may have a flow rate of only 50 ml/min which makes the monitor suitable for neonatal sampling.

In embodiments, a pocket-sized, fully quantitative capnometer may be provided. The capnometer may monitor carbon dioxide concentrations and respiratory rate in patients of all ages. The capnometer may use miniaturized mainstream EtCO2 technology. In an embodiment, the capnometer may weigh 2.1 oz. The capnometer may not need routine calibration. In an embodiment, the capnometer may be battery powered such as by two AAA batteries for continuous 8 hour long operation. The capnometer may be used for intubation verification, as an indicator for return of spontaneous circulation, routine airway management, ventilator transport, ventilator weaning, and the like.

The capnometer may provide EtCO2 and respiratory rate measurements in a fully quantitative numeric value on an LED user interface. Further, the capnometer may have an optional alarm preset for certain levels of EtCO2. The capnometer may include two ports. One of the two ports may connect to the airway connector and another port may connect to the ventilation system. The capnometer may be an effective noninvasive indicator of cardiac output, CPR effectiveness. Further, the capnometer may also indicate for return of spontaneous circulation during resuscitation of patients. The capnometer provides accuracy and is also easy to use in all areas of clinical practice.

In embodiments, the present invention may provide a capnography sensor (hereinafter referred as 'sensor'). The sensor may be a small, lightweight plug-and-play sensor that may be used with a R-series defibrillator. Further, a mainstream sensor may be used for mechanically ventilated patients and those patients that may be intubated that require intensive monitoring. The capnometer may provide $EtCO_2$ monitoring to verify correct placement of an endotracheal tube, position of the endotracheal tube, to assess the effectiveness of CPR, and to assess cardiac output in patients with pulse-less electrical activity. The mainstream sensor may be placed on top of an airway adapter that may be placed directly in the breathing circuit. The airway adapter may prevent the mainstream sensor from direct contact and contamination with patient secretions. This may also prevent clogging of sensor or the need for water traps. The capnometer may also display a printable capnogram on the defibrillator screen for easy identification of abnormal waveforms.

In embodiments, the oral capnometer 102 may be portable. The portable capnometer 102 may be useful in evaluating the respiratory condition of spontaneously breathing patients in hospitals and in in-home care. Further, the portable oral capnometer 102 may be used accurately in spontaneously breathing patients with or without chronic pulmonary diseases. The oral capnometer 102 may be slipped into a pocket. In an embodiment, the portable capnometer 102 may be powered by two AAA batteries and may not need calibration. The oral capnometer 102 may have a long battery life.

Further, the oral capnometer 102 may have multiple applications that may include but are not limited to intubation verification, an indicator for return of spontaneous circulation, routine airway management, ventilator transport, and weaning In embodiments, the portable capnometer 102 may be designed for adults and infants. Further, the portable capnometer 102 may include mainstream infrared technology that may enable rapid 'breath by breath' measurement of both End tidal C02 and Respiratory Rate. In an embodiment of the present invention, the oral capnometer 102 may include disposable airway adapters that may be used with or use with CO2 and respiration monitors.

In embodiments, the oral capnometer 102 may include an indicator 1008, and more specifically, the oral capnometer 102 may include a binary indicator. The binary indicator may be a visual indicator, an audio indicator, an audio-visual indicator, and the like. The binary indicator may be used to detect the presence of pulmonary embolism and pulmonary arterial hypertension in a patient. Further, the binary indicator may provide only two results, yes or no. For example, if the patient is suffering from pulmonary embolism, the indicator 1008 may provide an audio or a visual indication to indicate the presence of the disease. In case, the disease is not detected the binary indicator may not provide any indication.

It will be evident to a person skilled in the art that the oral capnometer 102 may indicate the presence as well as absence of a disease. For example, the oral capnometer 102 may include a light source that may produce a red and a green light. The red and the green light may provide indication of presence or absence of a disease respectively. In embodiments, the light source may display gradations of color. For example, the amount of red may be indicative of how much $CO_2$ is present, where a pink color may indicate low $CO_2$ levels and white may indicate no $CO_2$.

Further, the light source may be a light emitting diode (LED). However, it will be evident to a person skilled in the art that other light sources may be used instead of LEDs. In other embodiments, the color of the indicator light may be associated with the diagnosis.

In embodiments, the oral capnometer 102 may include a device such as a lab on chip device (hereinafter referred as device) that may integrate one or several laboratory functions on a single chip. The device may be used as a lung on a chip model. The lung on a chip model may include living, breathing human lung on a microchip. The device may be made using human lung and blood vessel cells which may predict absorption of airborne nano particles and mimic the inflammatory response triggered by microbial pathogens. Further, the device may be used to test the effects of environmental toxins, absorption of aerosolized therapeutics, and the safety and efficacy of new drugs.

In embodiments, pulmonary arterial hypertension (PAH) is a condition in which blood pressure in the arteries of the lungs (the pulmonary arteries) may be abnormally high. PAH may be diagnosed by conducting various tests that may include chest x-rays, electrocardiography, and echocardiography on a patient. The test results may provide clues for diagnosis. However, measurement of blood pressure in a right ventricle and a pulmonary artery may be needed for confirmation of PAH. Further, the tests may provide indications that may be helpful in treatment of PAH. Such indications may be known as clinical indications.

The clinical indications may enable a physician to prescribe a medicine to a patient. The clinical indications may be a simple and direct way to communicate with patients about their medicines. A few extra words may be added to their prescription to enhance communication. Firstly the reason for the medicine may be explained, for example, Atenolol® 'to prevent migraine'. In many cases, medicines may have a variety of uses and a precise reason may avoid confusion especially if the medicine insert leaflets are read. In case of PAH, medicines that may improve blood flow through the lungs may be helpful for patients suffering from PAH. In embodiments, a cause of sudden PAH may be pulmonary embolism. The oral capnometer 102 may be used to detect the presence of PAH at an earlier stage as would be described later with reference to FIGS. 10-19.

As stated above, the oral capnometer 102 may be used to detect the presence of PAH at an earlier stage such as described in embodiments below.

FIGS. 10-19 refer to an oral capnometer 1002 that may be used to detect the presence of PAH at an earlier stage.

Figure 10:
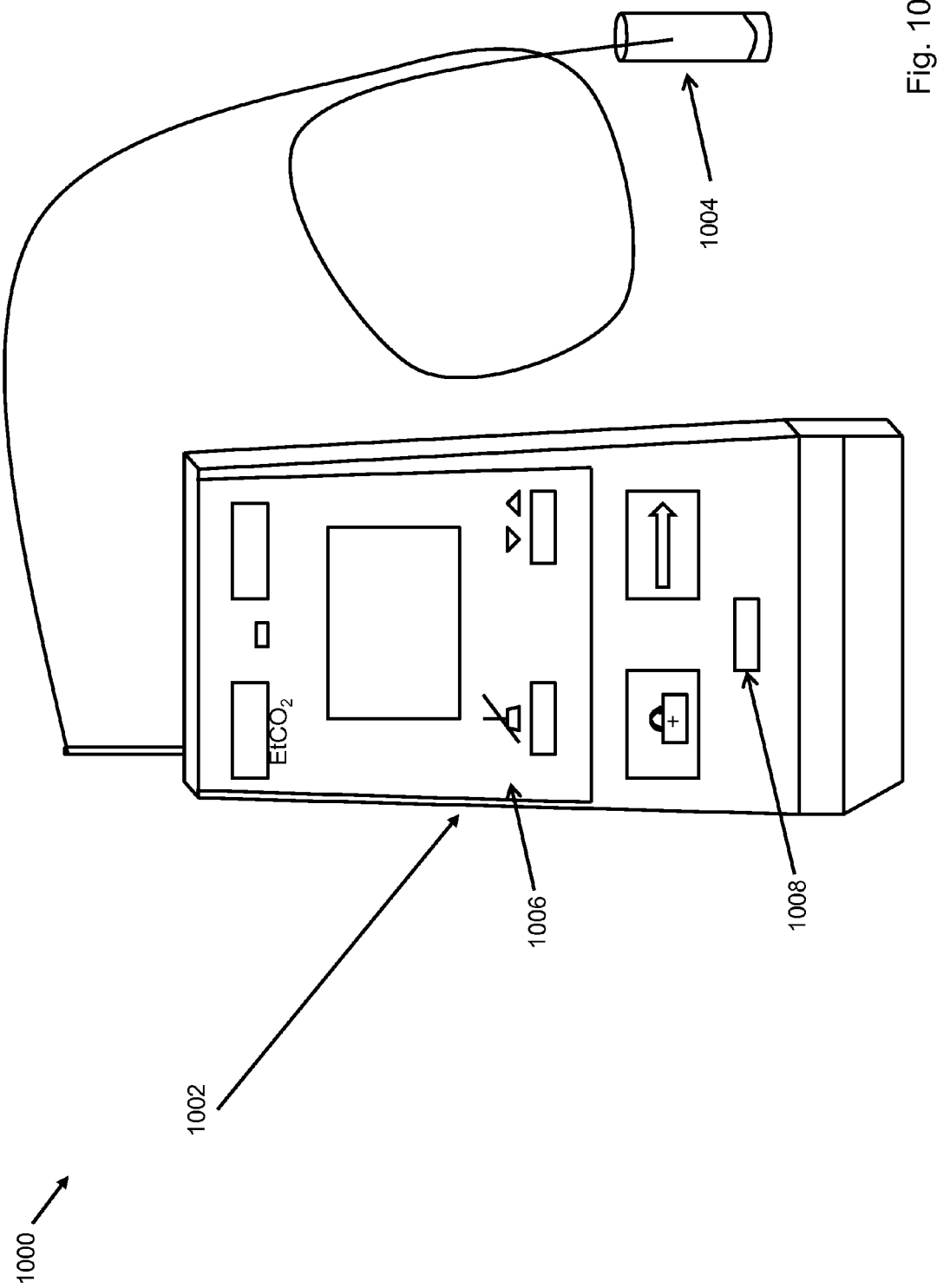
FIG. 10 depicts an image of a modified capnometer of the invention.

In an aspect, the oral capnometer 1002 may include an oral gas capture member 1004, an end tidal carbon dioxide detection device 1006 and an indicator 1008 as depicted in FIG. 10. The oral gas capture member 1004 may collect expired gases from the mouth to determine levels of expired carbon dioxide from the mouth of a subject. The end tidal carbon dioxide detection device 1006 may be attached to the oral gas capture member 1004 and may determine levels of the end tidal carbon dioxide at end expiration from the mouth of a subject. The end tidal carbon dioxide detection device may include a pressure sensor to determine pressure of the end tidal carbon dioxide. The indicator 1008 may be activated when the level of the end tidal carbon dioxide falls below a pre-determined threshold value.

In an aspect of the invention, the oral gas capture member 1004 may collect expired gases from the mouth of the patient at pre-determined regular intervals. In an aspect of the invention, the pressure sensor of the end tidal carbon dioxide detection device is a differential pressure sensor. In an aspect of the invention, the end tidal carbon dioxide detection device may be configured to detect pulmonary arterial hypertension. The end tidal carbon dioxide detection device may be used to measure partial pressure of expired gases collected in the oral gas capture member 1004. The measured partial pressure may be used for detection and diagnosis of pulmonary arterial hypertension (PAH).

In an aspect of the invention, the end tidal carbon dioxide detection device may be configured to detect a level of pulmonary arterial hypertension such that the level of pulmonary arterial hypertension may be monitored over a time interval as will be explained later by the way of FIGS. 14-17.

In an aspect, a study design may be created for measurement of the end tidal carbon dioxide. In embodiments, a measurement of the end tidal carbon dioxide (hereafter referred to as EtCO2) may be used to discriminate pulmonary hypertension (PH) patients with PAH and from those with diastolic dysfunction and passive PH. The measurement of the end tidal carbon dioxide may be used to determine the utility of this technique in the evaluation and treatment of the PH. Patients with well defined PH may be tested to determine the predictive value of EtCO2 in the differential diagnosis of the PH and the change of EtCO2 after a therapeutic change or an escalation. In an aspect, this disclosure describes a prospective, single center study designed to investigate the potential role of EtCO2 in the diagnosis of the PH.

In an aspect, a procedure may be conducted for setting controls (refers to the standard by which experimental observations may be evaluated. For example, in many clinical trials, a group of patients may be given an experimental drug or treatment, while the control group may be given a standard treatment for the illness) and determining population.

In an aspect, all new or returning patients aged ≥18 years of age, who were evaluated in the Vanderbilt University Center for Pulmonary Vascular Disease from August 2009 through March 2010, were eligible for enrollment. In an aspect, the PH may be defined as mean pulmonary artery pressure (mPAP) of 25 mmHg. The PAH may require a pulmonary artery occlusion pressure (PAOP) of 15 mmHg [30]. A PAOP-pulmonary artery diastolic (PAd) pressure difference of >11 mm for a diagnosis of PAH [40-43] had been measured. The patients with PVH had no other cause of PH identified after evaluation and had a PAOP >15 mmHg at rest and had increased PAOP >7 mmHg after infusion of 1L normal saline as previously described [43], or left atrial enlargement on echocardiography and mild-modest elevation in RVSP with no other etiology of PH found after standard evaluation and no identified risk factors for PAH. The RHCs (Right Heart Catheterization (RCHs) was performed as previously described [43]. The exclusion criteria included: ≥5 L/minute nasal cannula oxygen, portopulmonary hypertension (due to cirrhosis associated hyperventilation), serum bicarbonate >34 mmol/L, pregnancy, known neuromuscular disease, moderate or severe mitral stenosis, mitral or aortic regurgitation, left ventricular ejection fraction <55% by echocardiography, known hypercarbic respiratory failure, untreated hypo- or hyperthyroidism, hereditary hemorrhagic telangiectasia, uncertain diagnosis because of incomplete testing, diagnosis of WHO group 3 or 4 PH or mixed PH phenotype after thorough evaluation according to published guidelines [30].

Measurements

In an aspect, a procedure was conducted to measure EtCO2. EtCO2 was measured by a trained tester blinded to diagnosis using the Nellcor NPB 75 handheld capnograph (Mallinckrodt:Nellcor, St. Louis, Mo., USA) [44] with the oral gas capture member 1004 of this disclosure. Device calibration and oral modification may be performed as previously described [39]. EtCO2 measurements was recorded for five breaths after a patient or a subject may have rested for at least five minutes and upon completion of 6MWT (6 minute walk test) if performed [39]. Demographic data, results of blood values, 6MWT results, pulmonary function testing, and RHC data was extracted from the medical record. 6MWTs may be performed according to the American Thoracic Society (ATS) criteria [45].

Healthy Controls—Six Minute Walk Testing

The 6MWT was performed in 13 healthy controls (controls refer to control individuals as described above, age mean±SD, 30±7 years; 7 males) with EtCO2 recorded as above.

Determination of the Effects of PAH Treatment on ETCO2

In an aspect, a procedure was conducted for determining the effects of the PAH treatment on the EtCO2. The procedure involved measuring the effects of PAH treatment on EtCO2 among two groups of patients. The two groups of patients may be referred to as a first group and a second group. The first group of patients initiated treatment with an intravenous or subcutaneous prostaglandin followed by clinically prescribed dose uptitration, and the second group of patients received an intravenous or subcutaneous prostaglandin wherein a dose increase of >2 ng/kg/min of epoprostenol or treprostinil may be prescribed for treatment of worsening symptoms. EtCO2 was measured at a rest position of the subject or patient prior to and within three months of the therapeutic change. Poor clinical response was defined by death related to PAH or failure to improve one functional class or increase 6MWT distance by >10% [30, 46].

Statistical Analysis

In an aspect, a statistical analysis was undertaken to analyze the results obtained from the above procedures. Based on prior publications [43], a 60% positive rate had been assumed for PAH in subjects or patients for pulmonary vascular disease. In accordance with this rate and a standard deviation (SD) of 3 mmHg in EtCO2 measurements in normal volunteers, a sample size calculation determined that 102 patients was required to detect a difference in EtCO2 of 2 mmHg between groups with 90% power at $\alpha$-level (significance level) of 0.05. Continuous variables have been presented herein as mean±SD, unless otherwise noted, and had been analyzed using an unpaired t-test or Wilcoxon Rank Sum testing. The patients were enrolled only once, except for patients initiating or increasing the prostaglandin therapy. The effects of PAH therapy were analyzed using paired t-test. Categorical variables have been reported herein as percentages and had been analyzed using Fisher's exact test. The Receiver Operating Characteristic (ROC) curves with area under the curve (AUC) were generated for determining sensitivity and specificity of different EtCO2 cutoff levels in discrimination of PAH from patients without PAH. All p-values are two-tailed and values 0.05 considered significant. A data analyses has been performed using SPSS for Windows version 19.0 (SPSS Inc., Chicago, Ill.) and GraphPad Prism version 5.0c (LaJolla, Calif., USA).

Results

Study Patients

A set of results were obtained from above procedures and statistical analysis. In an aspect, the study conducted on patients had also been aimed at determining demographics of the patients and to study features of the patients without PH or severe pulmonary function tests (PTF) abnormalities. The results for this study have been described as follows in Table 4:

TABLE 4

Demography

|  | N = 7 |
|---|---|
| Age (years) | 52.1 ± 12.0 |
| Number Female (%) | 6 (86) |
| BMI (kg/m$^2$) | 33.6 ± 9.6 |
| Co-morbid conditions | |
| Diabetes Mellitus | 4 |
| Systemic hypertension | 5 |
| Hyperlipidemia | 3 |
| Pulmonary Function Tests | |
| DLCO (%) | 75.7 ± 23.9 |
| FEV1 (%) | 74.2 ± 12.4 |
| FVC (%) | 71.2 ± 13.7 |
| Plasma Bicarbonate (mmol/L) | 27.3 ± 2.7 |
| Six Minute Walk Distance (meters) | 452.3 ± 114.9 |
| Hemodynamic Data (5 patients) | |
| RAP (mmHg) | 4.2 ± 3.6 |
| mPAP (mmHg) | 17.6 ± 5.2 |
| PAOP or LAP (mmHg) | 9.4 ± 2.4 |
| CI (l/m/m$^2$) | 2.87 ± 0.9 |
| PVR (Wood units) | 1.4 ± 1.1 |
| PAd-PAOP (mmHg) | 0.4 ± 1.7 |

In an aspect, the data in the Table has been presented as mean±SD unless otherwise noted. Referring to Table 4 as presented herein, BMI refers to body mass index, DLCO refers to diffusing capacity of carbon monoxide, FEV1 refers to forced expiratory volume in one second, FVC refers to forced vital capacity, RAP refers to right atrial pressure, mPAP refers to mean pulmonary artery pressure, PAOP refers to pulmonary artery occlusion pressure, LAP refers to left atrial pressure, CI refers to cardiac index, PVR refers to pulmonary vascular resistance, and PAd refers to diastolic pulmonary artery pressure unless stated otherwise.

Figure 11A:
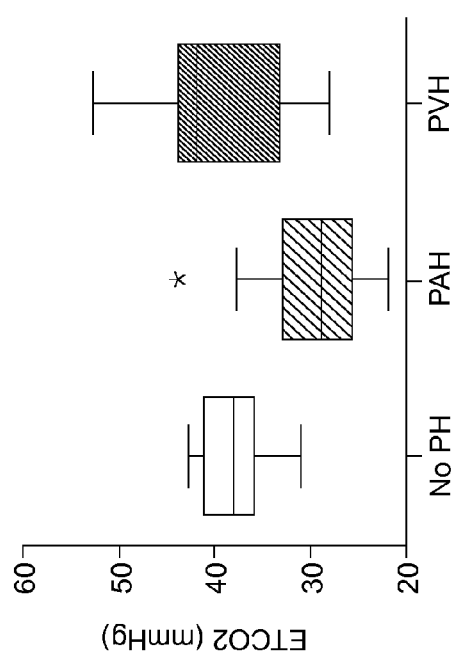
FIG. 11A depicts end tidal carbon dioxide performance characteristics and pulmonary arterial hypertension diagnosis.
Figure 11B:
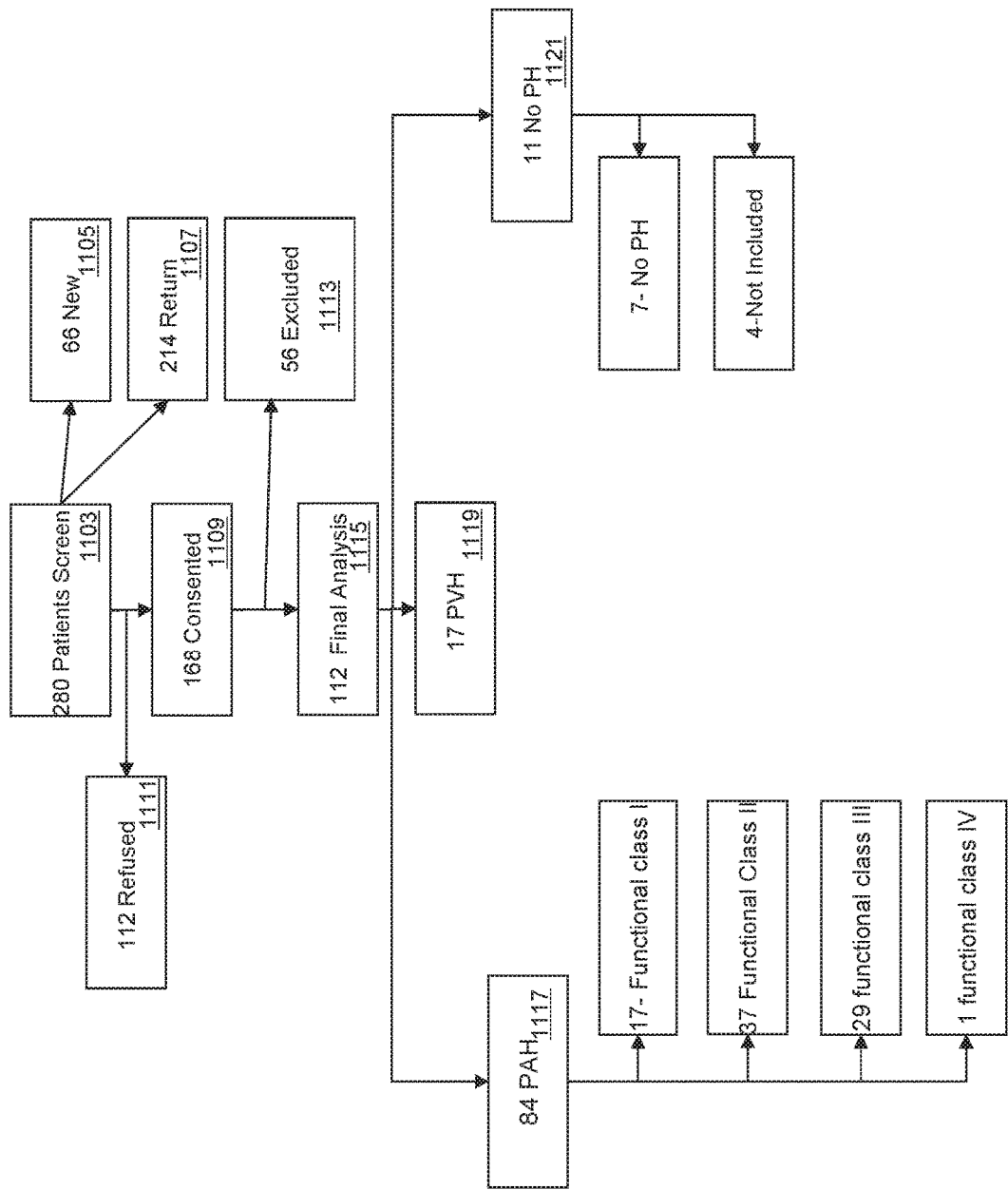
FIG. 11B depicts a study flow diagram.

Referring to Table 4 and FIG. 11B, demography of the evaluation is illustrated. At step 1103, 280 patients were evaluated for PH over the enrollment period; out of which, at step 1105, 66 new patients and, at step 1107, 214 were return patients. Out of 280, at step 1109, 168 patients consented to enrollment and at step 1111, 112 patients refused. At step 1113, fifty Six (56) patients were excluded due to portopulmonary hypertension (n=5), advanced parenchymal lung disease (n=5), non-group 1 or 2 PH (n=30), miscellaneous causes (HCO3>34 n=5, no final diagnosis n=3, incomplete data n=7, uncontrolled hyperthyroidism n=1), wherein n refers to number of patients. One hundred twelve (112) patients were included in the final analysis at step 1115. Eighty four (84) patients were diagnosed with PAH at step 1117, 17 patients with PVH at step 1119, and 11 patients were found to have no PH at step 1121. In an aspect, out of the 84 patients with PAH, 17 were from functional class I, 37 from functional class II, 29 from functional class III, and one from functional class IV. The functional classes referred herein are from the PAH diagnosis classification system developed by the World Health Organization (WHO). In an aspect, the causes for the PAH may include idiopathic (n=33), connective tissue disease (n=23), heritable PAH (n=7), congenital heart disease (n=15), and miscellaneous (n=6), wherein n refers to the number of patients. Seven out of eleven patients in the group were found to have no PH, and only had mild or moderate pulmonary function testing (PTF) abnormalities and normal chest imaging. These patients had been configured to constitute a control cohort (as referred to in Table 4). The remaining four patients with severely abnormal parenchyma were not included in the control group. The no PH group had a tendency to be obese and frequently had diabetes mellitus, systemic hypertension, and hyperlipidemia. The pulmonary function testing did not show severe impairment and 5 patients who had RHC (Right heart catheterization) data available, the mPAP and PAOP were shown to be in a normal range. Two patients, who did not have RHC, had normal physical examination and normal echocardiography.

End Tidal CO2 in PAH and PVH: As stated above, 84 patients had been diagnosed with PAH and 17 with PVH; these patients had been used for measurement of the EtCO2. A comparison was drawn between the measured EtCO2 values from the patients suffering from PAH, PVH and no PH. The comparison chart has been shown with reference to Table 5 below and comparison diagrams are illustrated in FIGS. 11A-11D. The data has been presented herein as median with 95% CI.

TABLE 5

Demographic Data in PAH Compared with PVH

|  | PAH (n = 84) | PVH (n = 17) | p Value |
|---|---|---|---|
| Age (years) | 50.5 ± 14.1 | 63.9 ± 12.2 | 0.0004 |
| Number Female (%) | 62 (73.8) | 12 (70.6) | 0.30 |
| Plasma Bicarbonate (mmol/L) | 25.7 ± 3.2 | 28.1 ± 2.4 | 0.007 |
| Hemodynamic Data (no. 84 PAH, 14 PVH) | | | |
| RAP (mmHg) | 7.5 ± 5.9 | 11.9 ± 5.8 | 0.01 |
| mPAP (mmHg) | 49.6 ± 15.8 | 38.6 ± 11.6 | 0.02 |
| PAOP or LAP (mmHg) | 9.0 ± 4.6 | 19.9 ± 6.9 | <0.0001 |
| CI (l/m/m$^2$) | 2.6 ± 0.9 | 3.3 ± 0.7 | 0.01 |
| PVR (Wood units) | 9.2 ± 5.0 | 3.4 ± 1.7 | 0.0001 |
| PAdiastolic-PAOP (mmHg) | 23.4 ± 11.2 | 4.4 ± 6.0 | <0.0001 |

In an aspect, the t-test was undertaken for continuous variables, chi-square test for nominal variables, Mann Whitney U test for ordinal variables. The BMI refers to body mass index, DLCO refers to diffusing capacity of carbon monoxide, RAP refers to right atrial pressure, mPAP refers to mean pulmonary artery pressure, PAOP refers to pulmonary artery occlusion pressure, LAP refers to left atrial pressure, CI refers to cardiac index, PVR refers to pulmonary vascular resistance, and PAd refers to diastolic pulmonary artery pressure unless stated otherwise.

In an aspect, the PVH patients were found to be older, but had a similar percentage of females. Plasma bicarbonate was higher in patients with PVH, but values were within the normal range. In patients with available RHC data, PAOP may confirm PVH or PAH, with a low gradient from the PA diastolic pressure to the pulmonary artery occlusion pressure (Pad-PAOP) in the PVH group. mPAP and PVR was significantly higher in PAH patients as compared to those with PVH.

The EtCO2 was compared between PAH, PVH, and no PH group as illustrated in FIG. 11A.

FIG. 11A depicts a mean EtCO2 in PAH, PVH, and no PH patients. Median EtCO2 was significantly lower in patients with PAH (29.0, 95% CI 28.3-30.4 mmHg) as compared with both no PH (38.0, 95% CI 34.4-41.6 mmHg) and PVH (41.9, 95% CI 36.6-43.4 mmHg, p<0.0001 PAH vs. both groups). A difference in EtCO2 between idiopathic or heritable PAH and connective tissue disease-associated PAH (data not shown) was not detected. EtCO2 in patients with no PH was not different from previously published normal mean EtCO2 in healthy controls [39].

Figure 12:
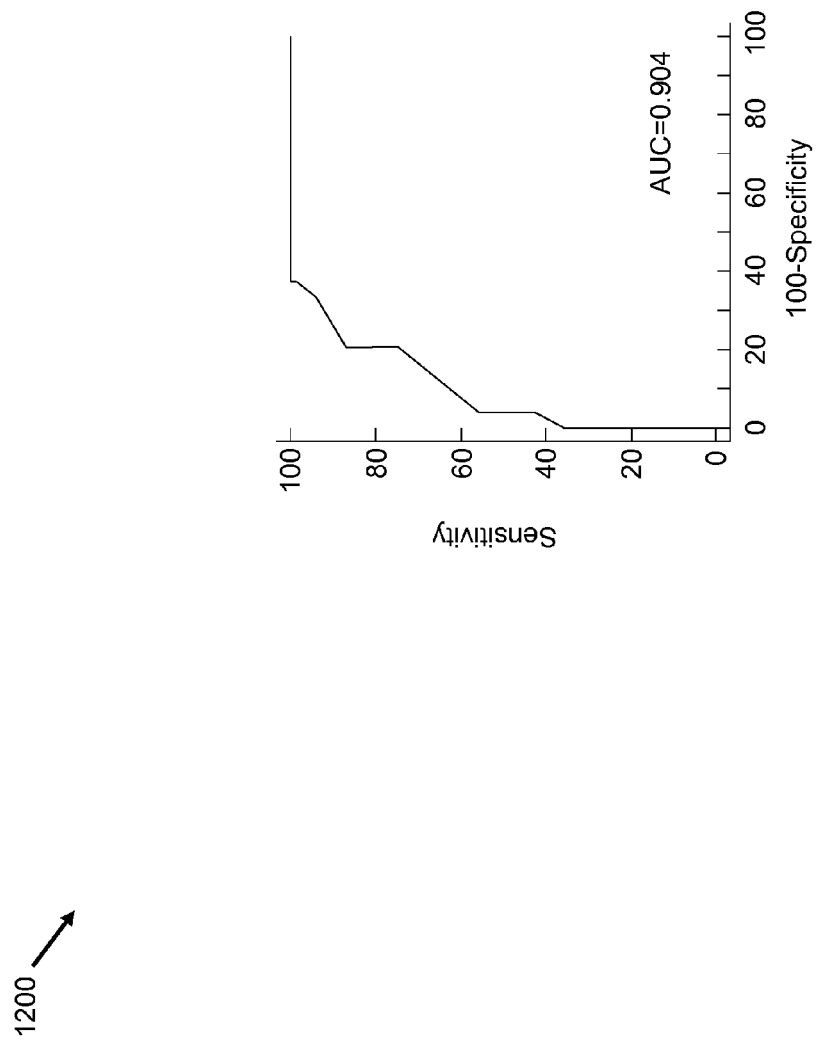
FIG. 12 depicts end tidal carbon dioxide characteristics and specificity of pulmonary arterial hypertension diagnosis.
Figure 13A:
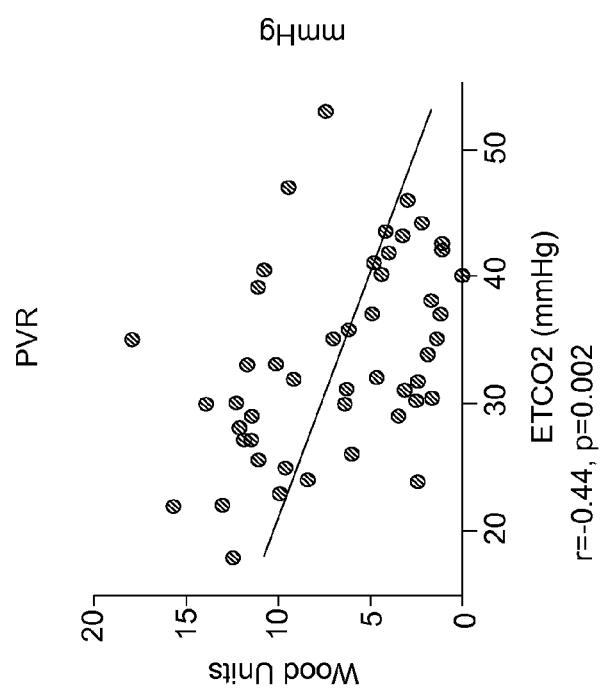
FIGS. 13A-13F depict correlation of end tidal carbon dioxide with other invasive hemodynamic procedures.
Figure 13B:
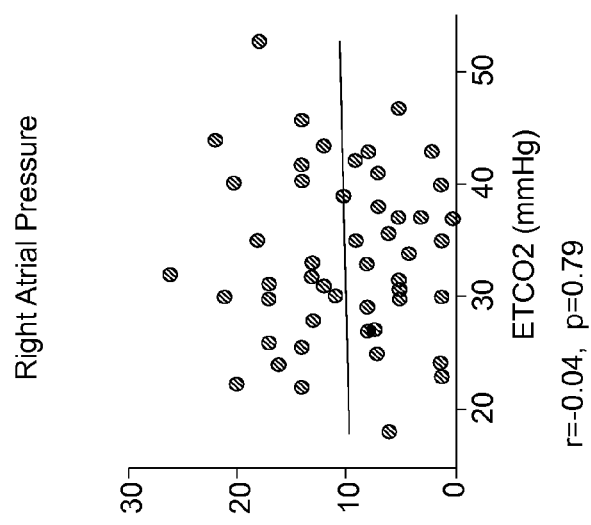
Figure 13C:
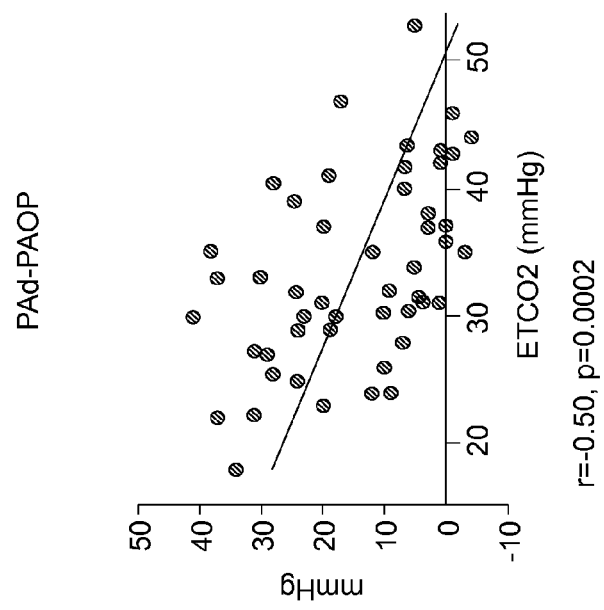
Figure 13D:
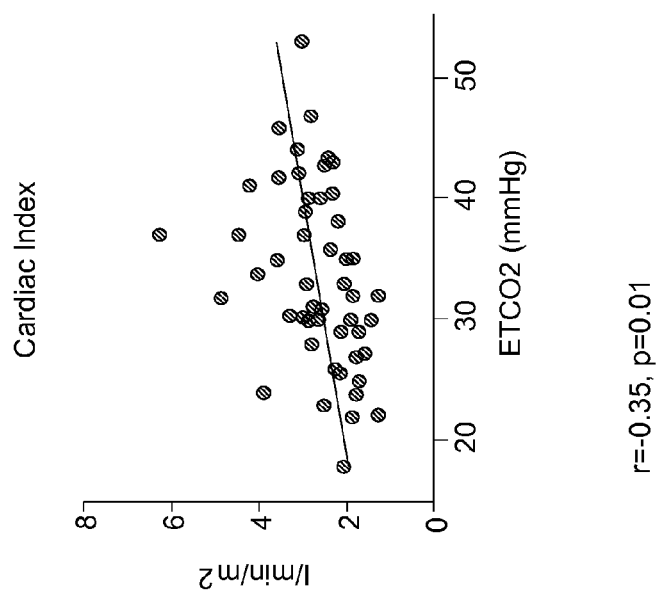
Figure 13E:
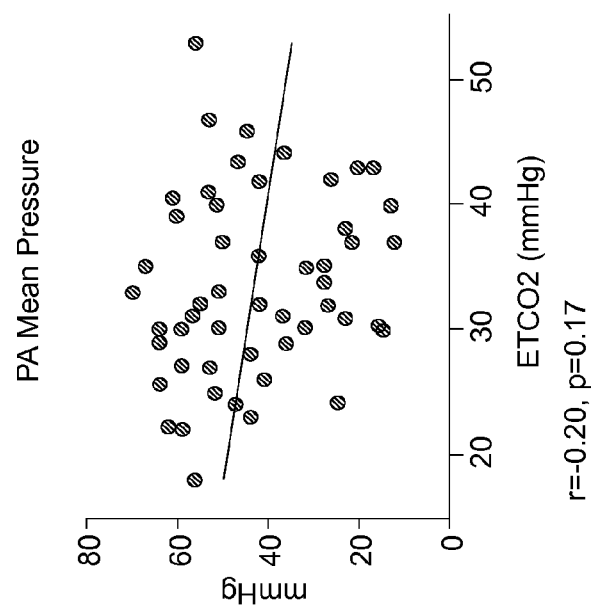
Figure 13F:
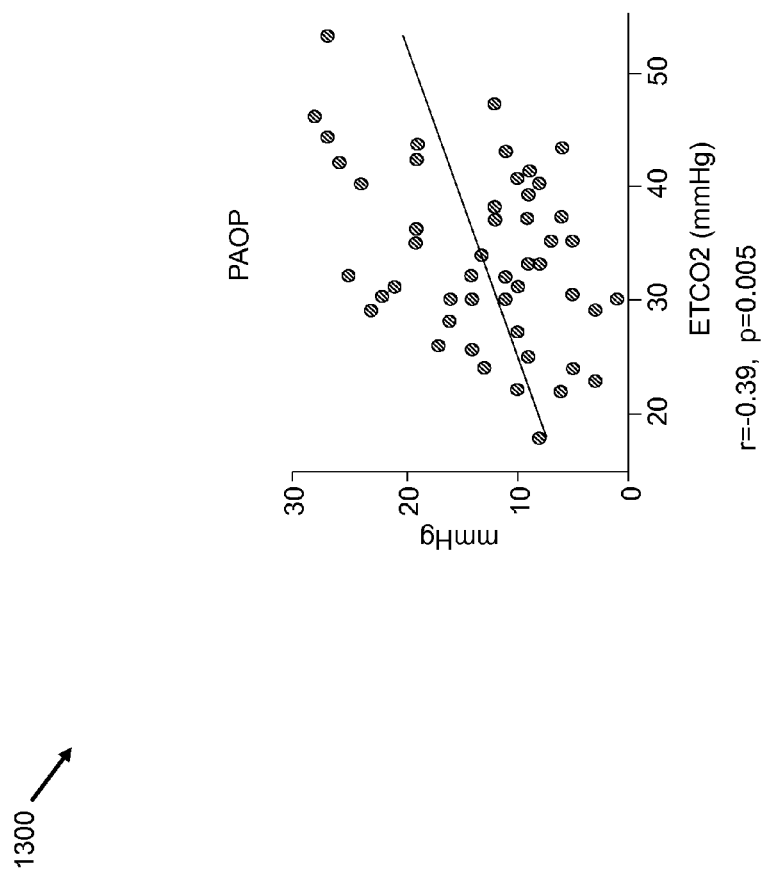

An ROC curve was generated evaluating EtCO2 to discriminate between PAH, no PH, and PVH (as depicted in FIG. 12). EtCO2 showed good performance characteristics with $r^2$ of 0.904. Sensitivities, specificities, and positive and negative predictive values of EtCO2 in detection of PAH are shown in Table 6.

TABLE 6

Sensitivity and Specificity of a Given Measurement of EtCO2

| Mean EtCO2, Positive if ≤ x mmHg | Sensitivity % | Specificity % | Positive Predictive Value % | Negative Predictive Value % |
|---|---|---|---|---|
| 28 | 42.9 | 95.8 | 97.3 | 32.4 |
| 30 | 60.7 | 91.7 | 96.2 | 40.0 |
| 32 | 75.0 | 79.2 | 92.6 | 47.5 |
| 34 | 86.9 | 79.2 | 93.5 | 63.3 |
| 36 | 91.7 | 70.8 | 91.6 | 70.8 |
| 38 | 98.8 | 62.5 | 90.2 | 93.5 |

FIGS. 13A-13F depict correlation 1300 of EtCO2 with Invasive Hemodynamics.

Correlation of ETCO2 with Invasive Hemodynamics

In an aspect, a study was undertaken to determine the EtCO2 correlation with invasive hemodynamic measurements differentiating PAH from PVH. 51 patients who had RHC within three months of EtCO2 measurement were taken for this evaluation. In an aspect, EtCO2 was correlated strongly with PAd-PAOP (p=0.0002, FIG. 13C) and also with CI (r=−0.35, p=0.01, FIG. 13D), PAOP (r=−0.39, p=0.005, FIG. 13F), and PVR (r=−0.44, p=0.002, FIG. 13A). In an aspect, these may be important components in the distinction between PAH and PVH. A correlation of EtCO2 was not observed with mean PA pressure (r=−0.20, p=0.17, FIG. 13E) or right atrial pressure (r=−0.04, p=0.79, FIG. 13B). In the same cohort of patients with RHC data, there was not a correlation between six minute walk distance and any RHC parameters (data not shown).

Change in ETCO2 vs. Change in 6 Minute Walk Distance

In an aspect, the procedures mentioned above measured a change in EtCO2 vs change in 6-minute walk distance.

In some embodiments, the end tidal carbon dioxide detection device may be configured to detect a level of pulmonary arterial hypertension such that the level of pulmonary arterial hypertension can be monitored over a time interval, such as over a treatment interval. This is explained with reference to FIGS. 14-17.

Figure 14:
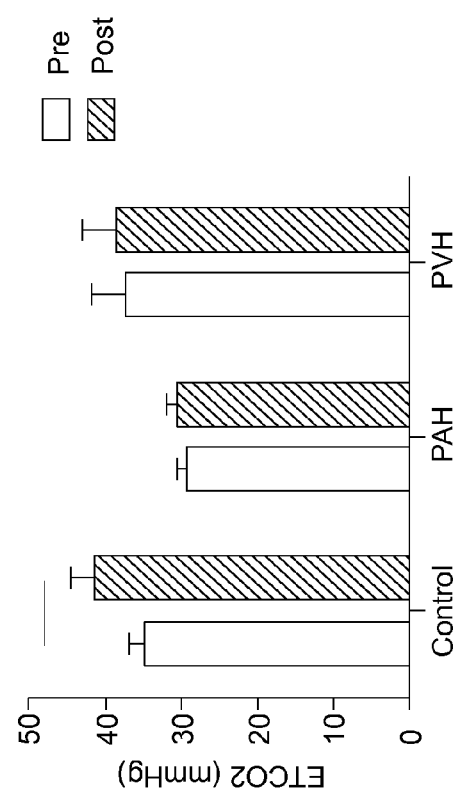
FIG. 14 depicts effects of testing parameters on measurement of end tidal carbon dioxide.
Figure 15A:
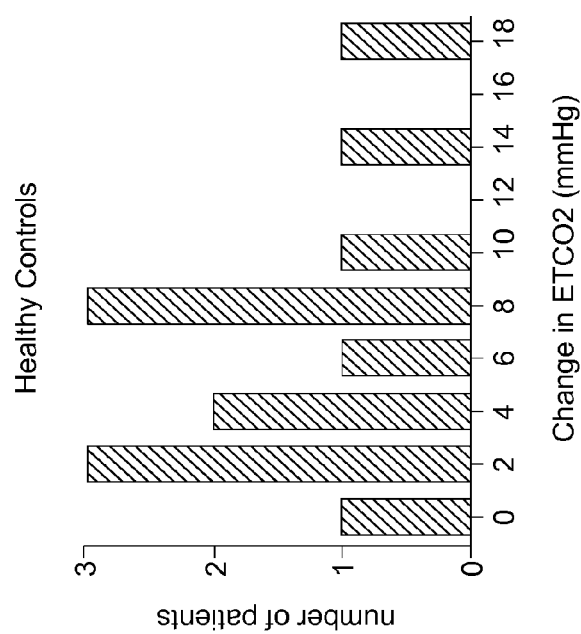
FIGS. 15A-15C depict effect of exercise on the ETCO2 in PAH, PVH, and non PH patients.
Figure 15B:
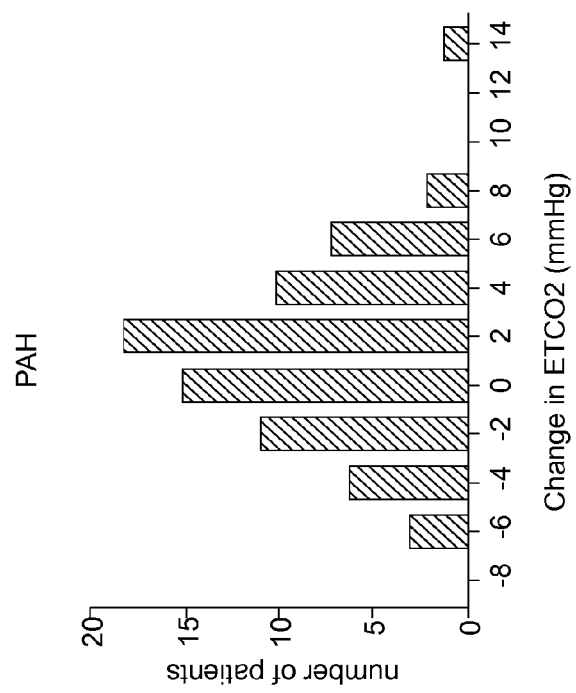
Figure 15C:
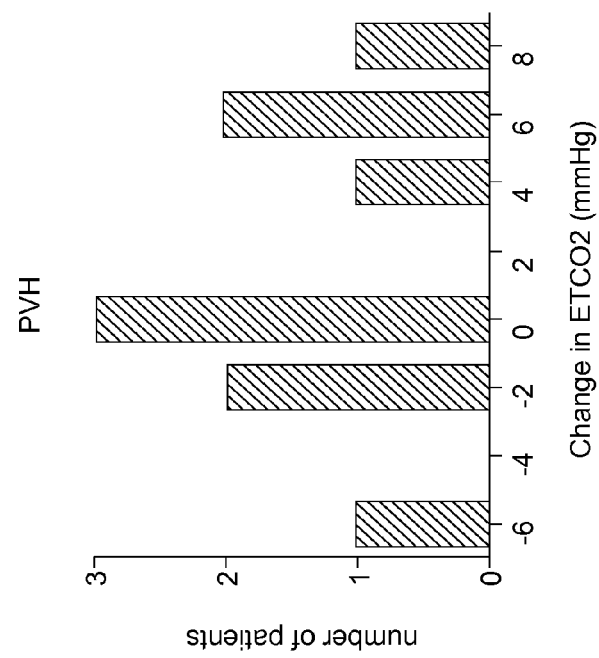
Figure 16:
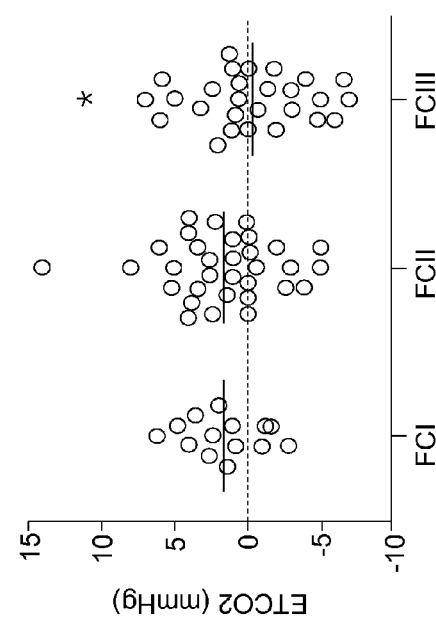
FIG. 16 depicts that PAH patients, who had functional class III, had decreased EtCO2 after 6MWT as compared to patients with functional class II.
Figure 17:
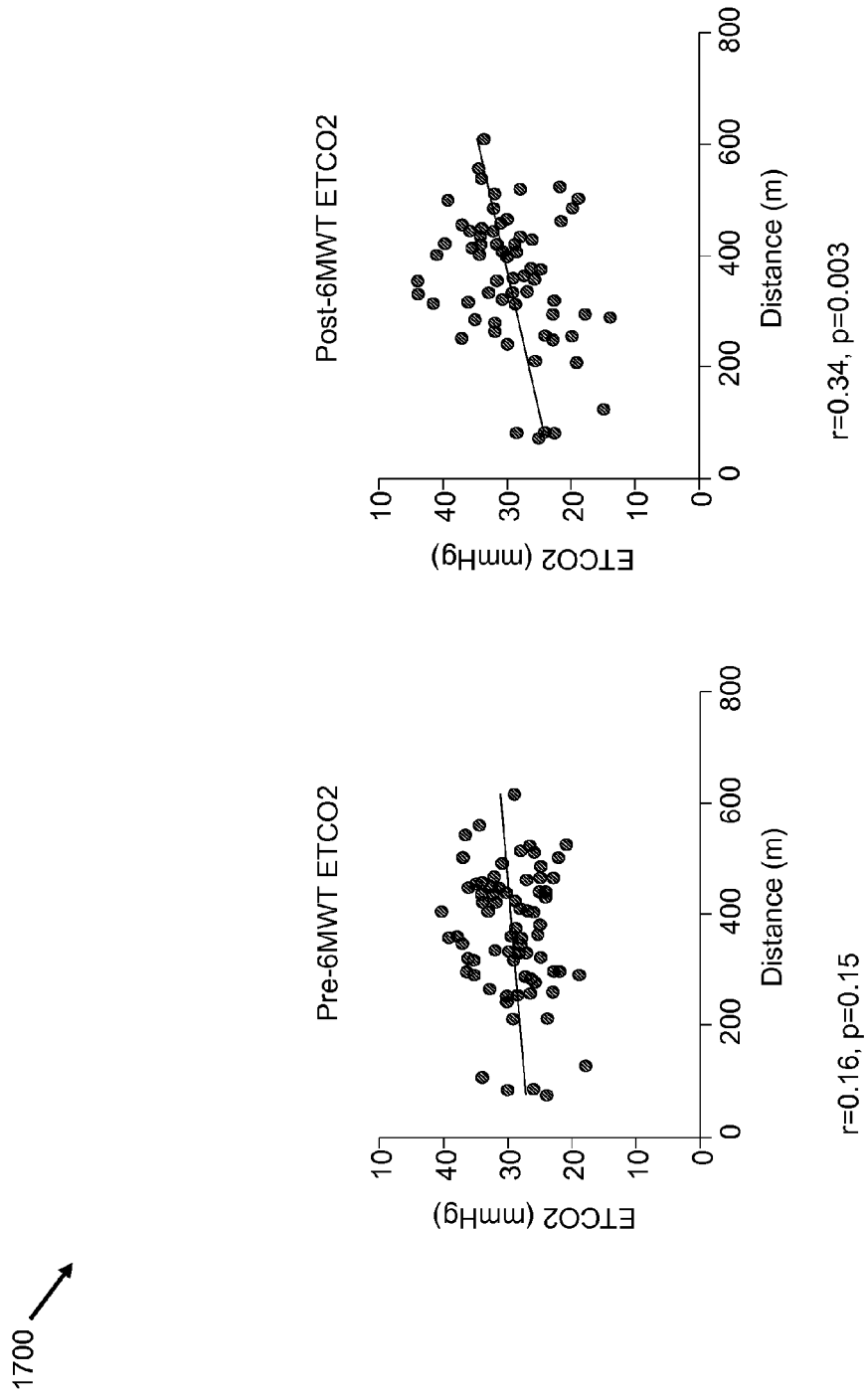
FIG. 17 depicts that in PAH patients, resting EtCO2 did not correlate with 6MWT distance.

In an aspect, the effect of 6MWT on EtCO2 may be compared in healthy volunteers, PAH and PVH patients in whom both resting and exercise data were available (n=13 healthy control, 73 PAH, 10 PVH, FIG. 14). In FIG. 14, bars denote p=0.0004, other comparisons were not significant. The data presented herein is reported with a mean with 95% CI. In healthy controls, EtCO2 increased after 6MWT [34, 47]. The mean value of EtCO2 did not increase in either PAH or PVH after exercise. The EtCO2 did not decrease in any healthy volunteer with exercise (FIGS. 15A-15C), EtCO2 decreased in PAH and PVH patients with exercise. PAH patients, who had functional class III, had decreased EtCO2 after 6MWT as compared to patients with functional class II (p=0.05, as depicted in FIG. 16). In an aspect, in PAH patients, resting EtCO2 did not correlate with 6MWT distance (as depicted in FIG. 17). In an aspect, EtCO2 correlated with 6MWT distance (r=0.34, p=0.003, n=73) after 6MWT.

Figure 18:
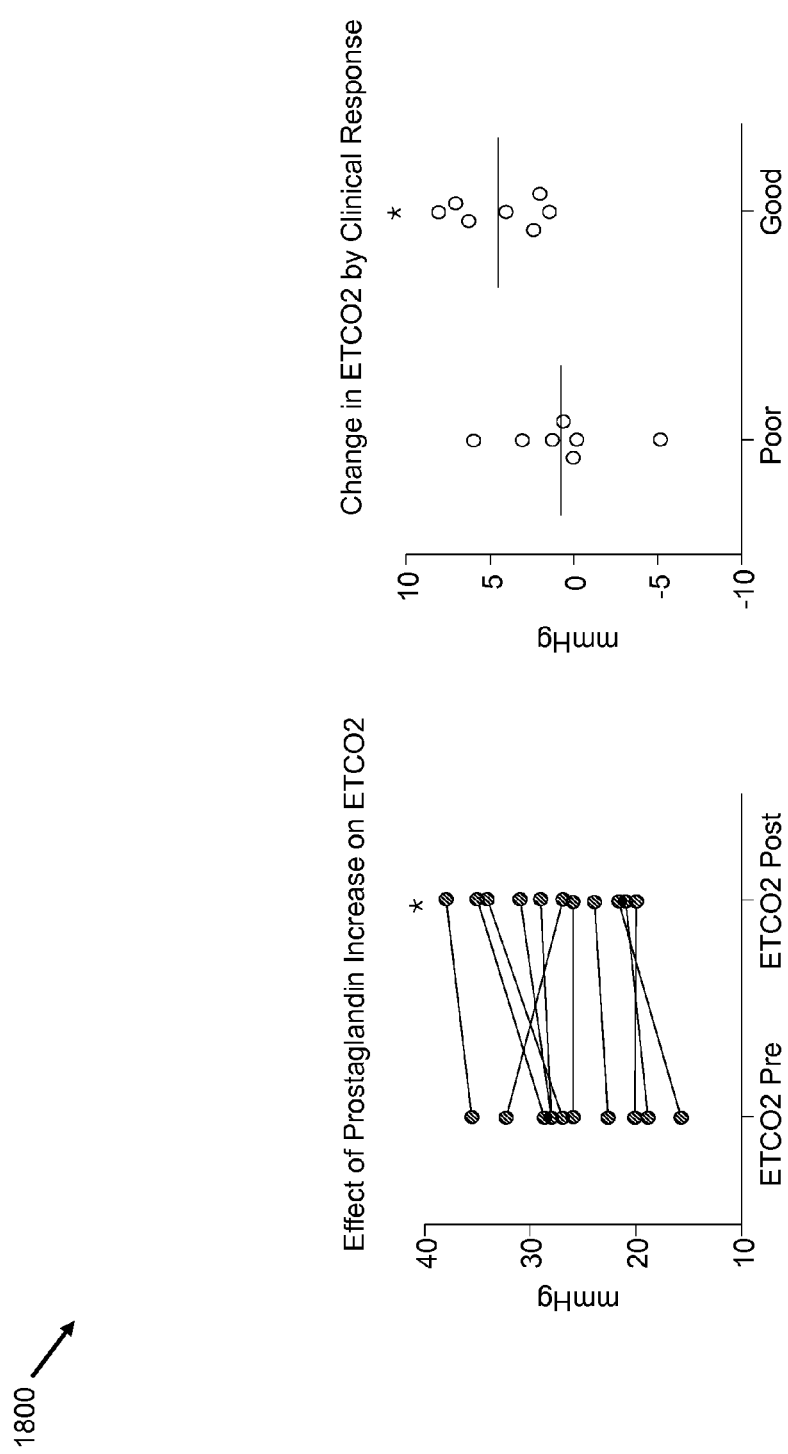
FIG. 18 depicts effects of therapy on pulmonary arterial hypertension.
Figure 19:
FIG. 19 depicts a flow chart of a method for diagnosing pulmonary arterial hypertension.
Figure 20:
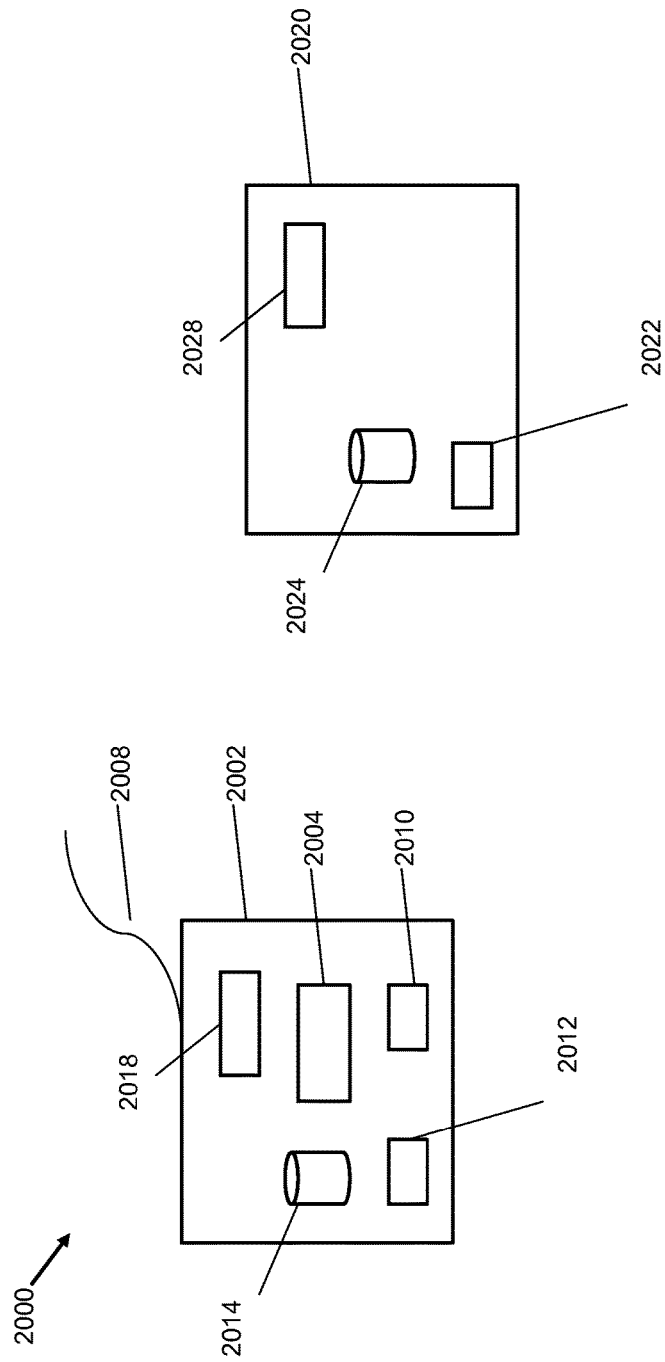
FIG. 20 depicts a system for measuring end tidal carbon dioxide.
Figure 21:
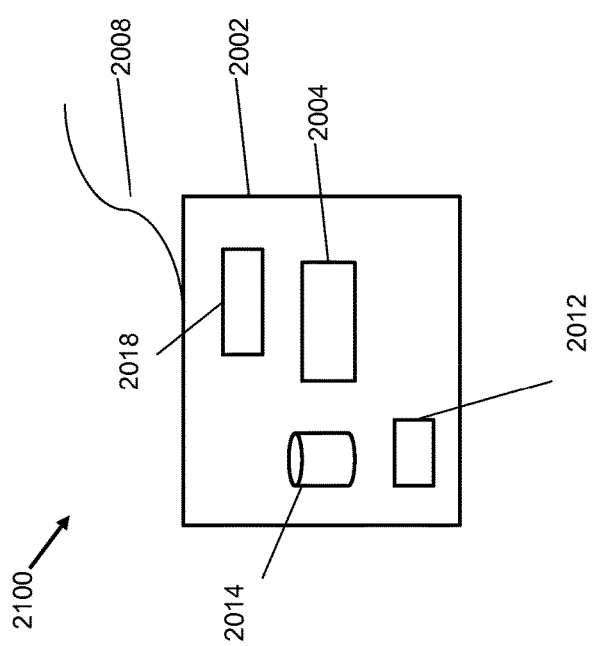
FIG. 21 depicts a device for measuring end tidal carbon dioxide.
Figure 22:
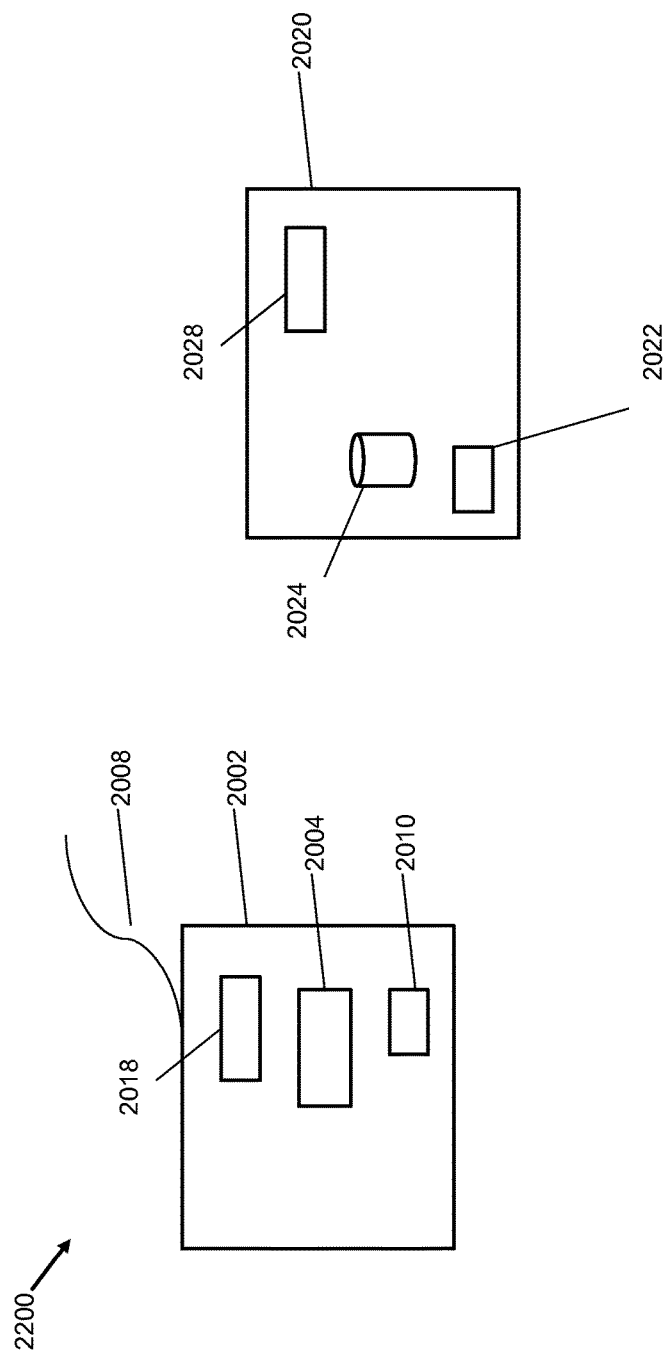
FIG. 22 depicts a system for measuring end tidal carbon dioxide.
Figure 23:
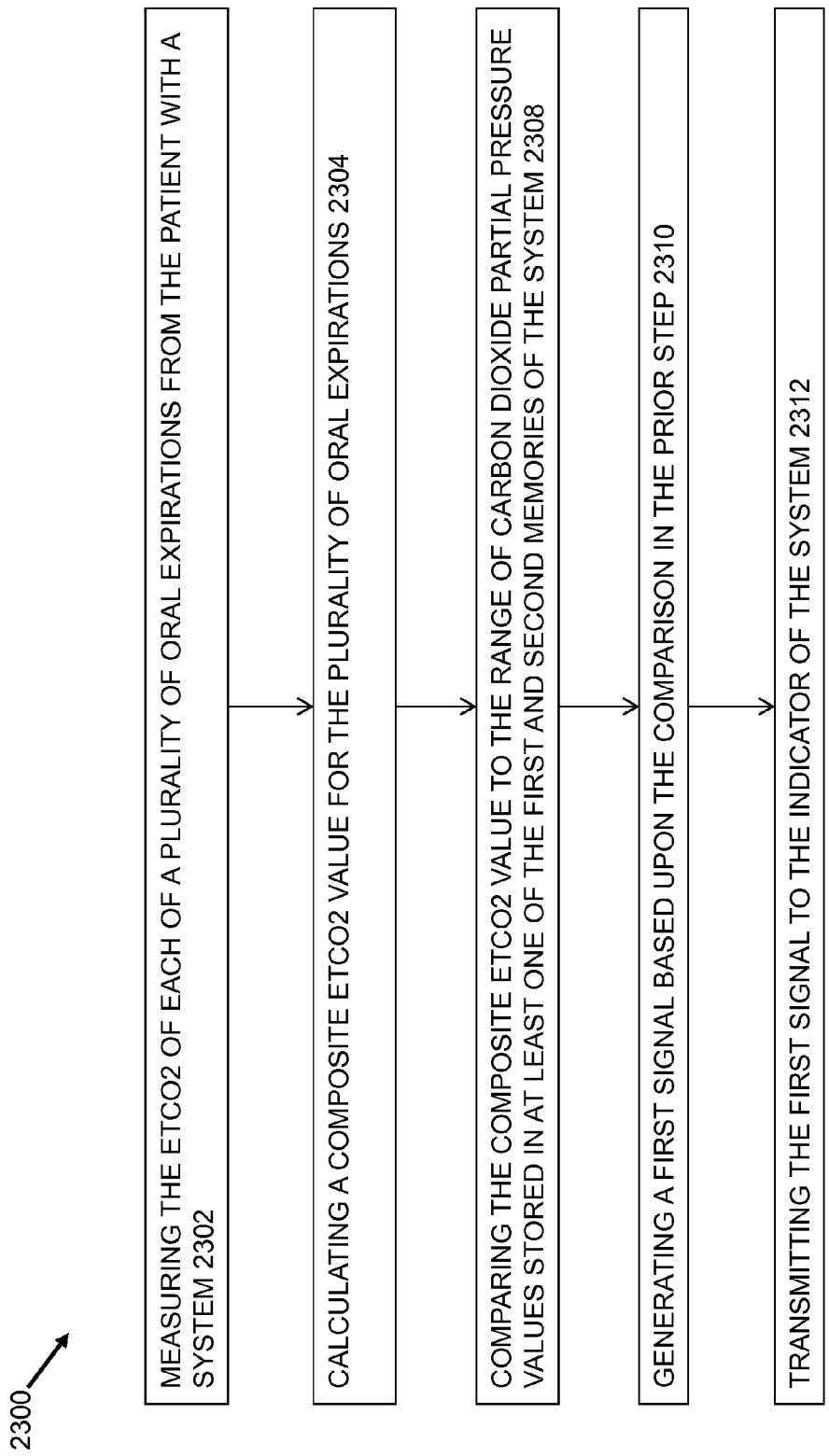
FIG. 23 depicts a flow chart of a method related to diagnosing pulmonary arterial hypertension.
Figure 24:
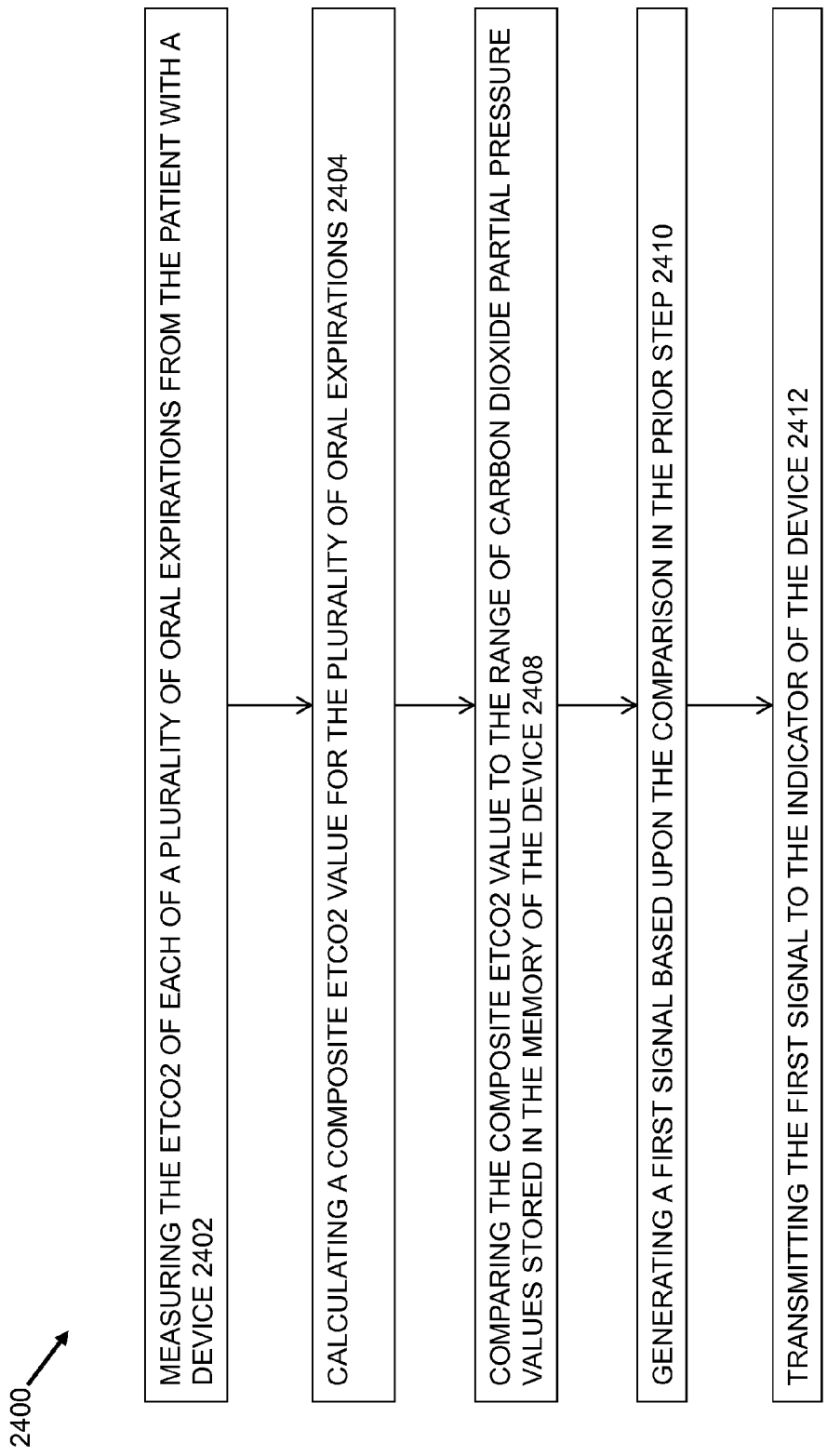
FIG. 24 depicts a flow chart of a method related to diagnosing pulmonary arterial hypertension.

In an aspect, the invention can be used to monitor the course of PAH therapy as mentioned above as the EtCO2 levels change with regard to the administration of drug therapy. FIG. 18 depicts the change and the phenomena as follows:

Change in ETCO2 with Prostaglandin Therapy

In an aspect, a change in EtCO2 with prostaglandin therapy may be measured to monitor the course of treatment of PAH. Fourteen (14) PAH patients (3 males, age 51±13 years, median follow up 11 months) either had begun prostaglandin therapy (n=7, all epoprostenol) or had an increase in the dose of prostaglandin to improve symptoms (n=7, 6=epoprostenol, 1=treprostinil SQ). The effects of this change in therapy are depicted in FIG. 18. In an aspect, the EtCO2 increased after therapy escalation with prostaglandin. FIG. 18 illustrates changes in EtCO2 in the group of patients treated with new or escalating doses of IV or subcutaneous prostaglandins shown on the left, p=0.03 paired t-test. The panel at left illustrates change in EtCO2 as a function of clinical response, p=0.04.

Seven patients were considered to have a poor response (3 patients died, one was referred for transplant, and two neither increased six minute walk distance by >10% nor improved one functional class). A change in EtCO2, after treatment, differentiated responders from non-responders (p=0.04).

These embodiments described a safe, simple, inexpensive measurement of EtCO2 at the bedside that may discriminate patients with PAH from those with PVH or no PH. EtCO2 may increase with clinical improvement following treatment of PAH, suggesting an improvement in perfusion in potentially obstructed vessels.

In the present study, resting bedside EtCO2 showed potential for a high negative predictive value ruling out PAH. In this cohort, the positive predictive value for EtCO2 38 mmHg was 90.2% and negative predictive value for EtCO2 >38 mmHg was 93.5%. If an EtCO2 cutoff of 38 mmHg were chosen in this cohort, we would spare 12/17 diagnostic RHCs for PVH, 3/7 for no PH and would have missed 3/84 patients with PAH. EtCO2 measurements had strong correlation with hemodynamic measurements for both the diagnosis of PAH (PAOP, PVR, Pad-PAOP gradient) and also correlated well with CI, an important measure in chronic follow up of patients with PAH, but did not correlate with right atrial pressure, a marker of right ventricular failure. These findings fit with the mechanism of depression of EtCO2 in PAH, pulmonary arterial obstruction, that would not be affected by right ventricular failure.

Investigators have shown a low EtCO2 in PAH patients and further decrease from baseline with cardiopulmonary exercise testing in PAH [34, 38, 47]; findings have been extended using the handheld capnograph 1000 of this disclosure and can be further correlated to the EtCO2 with hemodynamic markers of PAH as compared with PVH. The effect of 6MWT on EtCO2 in PAH was examined and it was found that change in EtCO2 was highly variable after exercise. In an aspect, it reflects the variety of functional classes enrolled in this study (as referred above as functional classes developed by WHO) as there may be a trend toward decrease in EtCO2 after exercise in functional class III patients, but not in functional classes I or II. In accordance with the variability in change in EtCO2 after 6MWT, focus has been on resting values for assessment of therapeutic response.

In an aspect, the EtCO2 may increase with clinically successful prostaglandin treatment for PAH. Six minute walk distance may not correlate with any invasive hemodynamic variable, therefore an improvement in EtCO2 may be a more useful surrogate hemodynamic marker in the follow up of PAH patients.

There may be a statistically significant difference in plasma bicarbonate between the patients with PVH and PAH. In an aspect, this may reflect diuretic use or renal compensation for differences in ventilation between the two groups (mentioned above as the first group and the second group). Arterial $PCO_2$ might identify a small number of low EtCO2 values that were false positives for PAH through alveolar hyperventilation.

In one aspect, the invention describes a method 1900. The method 1900 may include at step 1902 measuring a carbon dioxide content at end expiration to obtain an end tidal partial pressure of carbon dioxide in the subject. This can be done as described above.

At step, 1904, the method 1900 may include diagnosing pulmonary arterial hypertension when the level of the end tidal carbon dioxide measured falls below a pre-determined threshold value. This has been described with reference to FIGS. 10-18 and Tables 4-6 above.

In an embodiment, an oral capnometer may include an oral gas capture member that collects expired gases from the mouth, a carbon dioxide measuring device attached to the oral gas capture member that determines levels of end tidal carbon dioxide from the mouth of a subject, and an indicator that is activated when the level of carbon dioxide measured is below a pre-determined threshold, wherein the indicator is configured to activate when the level of the end tidal carbon dioxide falls below a threshold value indicative of a deadspace ventilation disease. The indicator may be at least one of a visual indicator, an audio indicator, an audio-visual indicator, and a binary indicator. The deadspace ventilation disease may be at least one of pulmonary arterial hypertension and pulmonary embolism. Carbon dioxide levels may be measured continuously. The indicator may be configured to deactivate when an end tidal carbon dioxide level rises above the pre-determined threshold indicating an improvement in the deadspace ventilation disease.

A method for diagnosis of pulmonary arterial hypertension may include the steps of measuring a carbon dioxide content at end expiration to obtain an end tidal partial pressure of carbon dioxide in the subject and diagnosing pulmonary arterial hypertension when the level of the end tidal carbon dioxide measured falls below a threshold value.

In an embodiment and referring to FIG. 10, a system 1000 for determining whether or not additional medical tests need to be conducted for the diagnosis of a pulmonary embolism or pulmonary arterial hypertension condition in a patient includes a housing 1002 and a carbon dioxide analyzer 1004 located at least partially within the housing 1002 and adapted to measure the partial pressure of carbon dioxide in a composite gas. A conduit 1008 is adapted to transfer an expiration from the patient's mouth to the carbon dioxide analyzer 1004. For example, the conduit 1008 may be a tubing attached to an oral adaptor. The system 1000 includes at least one of a first processor 1012 and a data transmitter 1010, the first processor 1012 being located within the housing 1002 and having a first memory 1014 operably associated therewith and the data transmitter 1010 being adapted to transmit data from the carbon dioxide analyzer 1004 to a second processor 1022, the second processor 1022 being located remotely from the housing 1002 and having a second memory 1024 operably associated therewith. A range of carbon dioxide partial pressure values may be stored in at least one of the first and second memories. An indicator 1018 may be associated with the first processor 1012 or an indicator 1028 may be associated with the second processor 1022. Either indicator 1018, 1028 may be adapted to respond to a signal from at least one of the first and second processors 1012, 1022 to provide an output in a human cognizable format. At least one of the first and second processors 1012, 1022 is adapted to compare a carbon dioxide partial pressure measurement from the carbon dioxide analyzer 1004 with the range of carbon dioxide partial values and to emit a signal to the indicator 1018, 1028, the signal being indicative of whether or not additional medical tests need to be conducted for the patient. Thus, the system 1000 includes a portion within the housing that receives gas for analysis but then can either transmit the analysis to a remote processor for comparison to a stored value or perform the comparison on-board.

Referring to FIG. 11, an embodiment of a standalone device 1100 may be used to determine whether or not additional medical tests need to be conducted for the diagnosis of a pulmonary embolism or pulmonary arterial hypertension condition in a patient. The device 1100 may include a housing 1002, a carbon dioxide analyzer 1004 located at least partially within the housing and adapted to measure the partial pressure of carbon dioxide in a composite gas, and a conduit 1008 adapted to transfer an expiration from the patient's mouth to the carbon dioxide analyzer 1004. A processor 1012 located within the housing 1002 and having a memory 1014 operably associated therewith, wherein a range of carbon dioxide partial pressure values are stored in the memory 1014. An indicator 1018 is adapted to respond to a signal from the processor to provide an output in a human cognizable format. The processor 1012 is adapted to compare a carbon dioxide partial pressure measurement from the carbon dioxide analyzer 1004 with the range of carbon dioxide partial pressure values and to emit a signal to the indicator 1018, the signal being indicative of whether or not additional medical tests need to be conducted for the patient.

In embodiments and referring to FIG. 12, a two-part system 1200 includes one part that receives expired gas for carbon dioxide analysis and transmits data using a data transmitter 1010 to a device or computer 1020 that contains a processor 1022 and memory 1024. The portion of the system 1200 that contains the data transmitter 1010 may not contain a processor or memory. The data transmitter 1010 may be a wireless or wired transmitter. In embodiments, a system 1200 for determining whether or not additional medical tests need to be conducted for the diagnosis of a pulmonary embolism or pulmonary arterial hypertension condition in a patient includes a housing 1002, a carbon dioxide analyzer 1004 located at least partially within the housing 1002 and adapted to measure the partial pressure of carbon dioxide in a composite gas, a conduit 1008 adapted to transfer an expiration from the patient's mouth to the carbon dioxide analyzer 1004, and a data transmitter 1010 adapted to transmit data from the carbon dioxide analyzer 1004 to a processor 1022, the processor 1022 being located remotely from the housing 1002 and having a memory 1024 operably associated therewith. A range of carbon dioxide partial pressure values are stored in the memory 1024 and an indicator 1018, 1028 is adapted to respond to a signal from the processor 1022 to provide an output in a human cognizable format. The processor 1022 is adapted to compare a carbon dioxide partial pressure measurement from the carbon dioxide analyzer 1004 with the range of carbon dioxide partial values and to emit a signal to the indicator 1018, 1028,the signal being indicative of whether or not additional medical tests need to be conducted for the patient. Thus, the system 1200 includes a portion within the housing that receives gas for analysis and then transmits the analysis to a remote processor for comparison to a stored value.

In an embodiment and referring to FIG. 13, a method for determining whether or not additional medical tests need to be conducted for the diagnosis of a pulmonary embolism or pulmonary arterial hypertension condition in a patient includes the step of measuring the EtCO2 of each of a plurality of oral expirations from the patient with a system 1302 including a housing, a carbon dioxide analyzer located at least partially within the housing and adapted to measure the partial pressure of carbon dioxide in a composite gas, a conduit adapted to transfer an expiration from the patient's mouth to the carbon dioxide analyzer, at least one of a first processor and a data transmitter, the first processor being located within the housing and having a first memory operably associated therewith and the data transmitter being adapted to transmit data from the carbon dioxide analyzer to a second processor, the second processor being located remotely from the housing and having a second memory operably associated therewith, a range of carbon dioxide partial pressure values stored in at least one of the first and second memories, and an indicator adapted to respond to a signal from at least one of the first and second processors to provide an output in a human cognizable format, wherein at least one of the first and second processors is adapted to compare a carbon dioxide partial pressure measurement from the carbon dioxide analyzer with the range of carbon dioxide partial values and to emit a signal to the indicator, the signal being indicative of whether or not additional medical tests need to be conducted for the patient. The method further includes calculating a composite EtCO2 value for the plurality of oral expirations 1304, comparing the composite EtCO2 value to the range of carbon dioxide partial pressure values stored in at least one of the first and second memories of the system 1308, generating a first signal based upon the comparison 1310, and transmitting the first signal to the indicator of the system 1312.

In an embodiment and referring to FIG. 14, a method for determining whether or not additional medical tests need to be conducted for the diagnosis of a pulmonary embolism or pulmonary arterial hypertension condition in a patient includes the step of measuring the EtCO2 of each of a plurality of oral expirations from the patient with a device 1402 including a housing, a carbon dioxide analyzer located at least partially within the housing and adapted to measure the partial pressure of carbon dioxide in a composite gas, a conduit adapted to transfer an expiration from the patient's mouth to the carbon dioxide analyzer, a first processor located within the housing and having a memory operably associated therewith, a range of carbon dioxide partial pressure values stored in the memory, and an indicator adapted to respond to a signal from the processor to provide an output in a human cognizable format, wherein the processor is adapted to compare a carbon dioxide partial pressure measurement from the carbon dioxide analyzer with the range of carbon dioxide partial pressure values and to emit a signal to the indicator, the signal being indicative of whether or not additional medical tests need to be conducted for the patient. The method further includes calculating a composite EtCO2 value for the plurality of oral expirations 1404, comparing the composite EtCO2 value to the range of carbon dioxide partial pressure values stored in the memory of the device 1408, generating a first signal based upon the comparison 1410, and transmitting the first signal to the indicator of the device.

In embodiments and referring to FIG. 15, a method for determining whether or not additional medical tests need to be conducted for the diagnosis of a pulmonary embolism or pulmonary arterial hypertension condition in a patient may include the step of measuring the EtCO2 of each of a plurality of oral expirations from the patient with a system 1502 including a housing, a carbon dioxide analyzer located at least partially within the housing and adapted to measure the partial pressure of carbon dioxide in a composite gas, a conduit adapted to transfer an expiration from the patient's mouth to the carbon dioxide analyzer, and a data transmitter adapted to transmit data from the carbon dioxide analyzer to a processor, the processor being located remotely from the housing and having a memory operably associated therewith. A range of carbon dioxide partial pressure values may be stored in the memory. An indicator may be adapted to respond to a signal from the processor to provide an output in a human cognizable format. The processor may be adapted to compare a carbon dioxide partial pressure measurement from the carbon dioxide analyzer with the range of carbon dioxide partial values and to emit a signal to the indicator, the signal being indicative of whether or not additional medical tests need to be conducted for the patient. The method further includes calculating a composite EtCO2 value for the plurality of oral expirations 1504, comparing the composite EtCO2 value to the range of carbon dioxide partial pressure values stored in the memory of the system 1508, generating a first signal based upon the comparison 1510, and transmitting the first signal to the indicator of the system 1512.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

The methods and systems described herein may be deployed in part or in whole through a machine that executes computer software, program codes, and/or instructions on a processor. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

Literature Cited:
1. Tapson V F. Acute pulmonary embolism. *N Engl J Med* 2008: 358(10): 1037-1052.
2. DeMonaco N A, Dang Q, Kapoor W N, Ragni M V. Pulmonary embolism incidence is increasing with use of spiral computed tomography. *Am J Med* 2008: 121(7): 611-617.
3. Parfrey P S, Griffiths S M, Barrett B J, Paul M D, Genge M, Withers J, Farid N, McManamon P J. Contrast material-induced renal failure in patients with diabetes mellitus, renal insufficiency, or both. A prospective controlled study. *N Engl J Med* 1989: 320(3): 143-149.
4. Brenner D J, Hall E J. Computed tomography—an increasing source of radiation exposure. *N Engl JMed* 2007: 357(22): 2277-2284.
5. Di Nisio M, Squizzato A, Rutjes A W, Buller H R, Zwinderman A H, Bossuyt P M. Diagnostic accuracy of D-dimer test for exclusion of venous thromboembolism: a systematic review. *J Thromb Haemost* 2007: 5(2): 296-304.
6. Wells P S, Anderson D R, Rodger M, Stiell I, Dreyer J F, Barnes D, Forgie M, Kovacs G, Ward J, Kovacs M J. Excluding pulmonary embolism at the bedside without diagnostic imaging: management of patients with suspected pulmonary embolism presenting to the emergency department by using a simple clinical model and d-dimer. *Ann Intern Med* 2001: 135(2): 98-107.
7. Perrier A, Roy P M, Sanchez O, Le Gal G, Meyer G, Gourdier A L, Furber A, Revel M P, Howarth N, Davido A, Bounameaux H. Multidetector-row computed tomography in suspected pulmonary embolism. *N Engl J Med* 2005: 352(17): 1760-1768.

8. Stein P D, Fowler S E, Goodman L R, Gottschalk A, Hales C A, Hull R D, Leeper K V, Jr., Popovich J, Jr., Quinn D A, Sos T A, Sostman H D, Tapson V F, Wakefield T W, Weg J G, Woodard P K. Multidetector computed tomography for acute pulmonary embolism. *N Engl J Med* 2006: 354(22): 2317-2327.
9. Amis E S, Jr., Butler P F, Applegate K E, Birnbaum S B, Brateman L F, Hevezi J M, Mettler F A, Morin R L, Pentecost M J, Smith G G, Strauss K J, Zeman R K. American College of Radiology white paper on radiation dose in medicine. *J Am Coll Radiol* 2007: 4(5): 272-284.
10. Miniati M, Bottai M, Monti S, Salvadori M, Serasini L, Passera M. Simple and accurate prediction of the clinical probability of pulmonary embolism. *Am J Respir Crit Care Med* 2008: 178(3): 290-294.
11. Kline J A, Meek S, Boudrow D, Warner D, Colucciello S. Use of the alveolar dead space fraction (Vd/Vt) and plasma D-dimers to exclude acute pulmonary embolism in ambulatory patients. *Acad Emerg Med* 1997: 4(9): 856-863.
12. Verschuren F, Liistro G, Coffeng R, Thys F, Roeseler J, Zech F, Reynaert M. Volumetric capnography as a screening test for pulmonary embolism in the emergency department. *Chest* 2004: 125(3): 841-850.
13. Robin E D, Julian D G, Travis D M, Crump C H. A physiologic approach to the diagnosis of acute pulmonary embolism. *N Engl J Med* 1959: 260(12): 586-591.
14. Rodger M A, Bredeson C N, Jones G, Rasuli P, Raymond F, Clement A M, Karovitch A, Brunette H, Makropoulos D, Reardon M, Stiell I, Nair R, Wells P S. The bedside investigation of pulmonary embolism diagnosis study: a double-blind randomized controlled trial comparing combinations of 3 bedside tests vs ventilation-perfusion scan for the initial investigation of suspected pulmonary embolism. *Arch Intern Med* 2006: 166(2): 181-187.
15. Manual O. Operators Manual. NPB 75: Portable bedside capnograph/pulse oximeter. Nellcor Puritan Bennet, Pleasonton, Calif., 1998.
16. Lehman C M, Wilson L W, Rodgers G M. Analytic validation and clinical evaluation of the STA LIATEST immunoturbidimetric D-dimer assay for the diagnosis of disseminated intravascular coagulation. *Am J Clin Pathol* 2004: 122(2): 178-184.
17. Value of the ventilation/perfusion scan in acute pulmonary embolism. Results of the prospective investigation of pulmonary embolism diagnosis (PIOPED). The PIOPED Investigators. *JAMA* 1990: 263(20): 2753-2759.
18. Kline J A, Israel E G, Michelson E A, O'Neil B J, Plewa M C, Portelli D C. Diagnostic accuracy of a bedside D-dimer assay and alveolar dead-space measurement for rapid exclusion of pulmonary embolism: a multicenter study. *JAMA* 2001: 285(6): 761-768.
19. Stein P D, Hull R D, Patel K C, Olson R E, Ghali W A, Brant R, Biel R K, Bharadia V, Kalra N K. D-dimer for the exclusion of acute venous thrombosis and pulmonary embolism: a systematic review. *Ann Intern Med* 2004: 140(8): 589-602.
20. Siragusa S, Terulla V, Pirrelli S, Porta C, Falaschi F, Anastasio R, Guarnone R, Scarabelli M, Odero A, Bressan M A. A rapid D-dimer assay in patients presenting at the emergency room with suspected acute venous thrombosis: accuracy and relation to clinical variables. *Haematologica* 2001: 86(8): 856-861.
21. Anderson D R, Kovacs M J, Dennie C, Kovacs G, Stiell I, Dreyer J, McCarron B, Pleasance S, Burton E, Cartier Y, Wells P S. Use of spiral computed tomography contrast angiography and ultrasonography to exclude the diagnosis of pulmonary embolism in the emergency department. *J Emerg Med* 2005: 29(4): 399-404.
22. Strzelczyk J J, Damilakis J, Marx M V, Macura K J. Facts and controversies about radiation exposure, part 2: low-level exposures and cancer risk. *J Am Coll Radiol* 2007: 4(1): 32-39.
23. Strzelczyk J J, Damilakis J, Marx M V, Macura K J. Facts and controversies about radiation exposure, part 1: controlling unnecessary radiation exposures. *J Am Coll Radiol* 2006: 3(12): 924-931.
24. Coche E, Vynckier S, Octave-Prignot M. Pulmonary embolism: radiation dose with multi-detector row CT and digital angiography for diagnosis. *Radiology* 2006: 240 (3): 690-697.
25. Stein P D, Woodard P K, Weg J G, Wakefield T W, Tapson V F, Sostman H D, Sos T A, Quinn D A, Leeper K V, Jr., Hull R D, Hales C A, Gottschalk A, Goodman L R, Fowler S E, Buckley J D. Diagnostic pathways in acute pulmonary embolism: recommendations of the PIOPED II Investigators. *Radiology* 2007: 242(1): 15-21.
26. van Belle A, Buller H R, Huisman M V, Huisman P M, Kaasjager K, Kamphuisen P W, Kramer M H, Kruip M J, Kwakkel-van Erp J M, Leebeek F W, Nijkeuter M, Prins M H, Sohne M, Tick L W. Effectiveness of managing suspected pulmonary embolism using an algorithm combining clinical probability, D-dimer testing, and computed tomography. *JAMA* 2006: 295(2): 172-179.
27. Yap K S, Kalff V, Turlakow A, Kelly M J. A prospective reassessment of the utility of the Wells score in identifying pulmonary embolism. *Med J Aust* 2007: 187(6): 333-336. 28

McLaughlin V V, Archer S L, Badesch D B, et al. ACCF/AHA 2009 expert consensus document on pulmonary hypertension a report of the American College of Cardiology Foundation Task Force on Expert Consensus Documents and the American Heart Association developed in collaboration with the American College of Chest Physicians; American Thoracic Society, Inc.; and the Pulmonary Hypertension Association. J Am Coll Cardiol 2009; 53:1573-1619
29 Hemnes A R, Forfia P R, Champion H C. Assessment of pulmonary vasculature and right heart by invasive haemodynamics and echocardiography. Int J Clin Pract Suppl 2009:4-19
30 Badesch D B, Champion H C, Sanchez M A, et al. Diagnosis and assessment of pulmonary arterial hypertension. J Am Coll Cardiol 2009; 54:S55-66
31 Arkles J S, Opotowsky A R, Ojeda J, et al. Shape of the right ventricular Doppler envelope predicts hemodynamics and right heart function in pulmonary hypertension. Am J Respir Crit Care Med 2011; 183:268-276
32 Peacock A, Keogh A, Humbert M. Endpoints in pulmonary arterial hypertension: the role of clinical worsening. Curr Opin Pulm Med 2010; 16 Suppl 1:S1-9
33 Pietra G G, Capron F, Stewart S, et al. Pathologic assessment of vasculopathies in pulmonary hypertension. J Am Coll Cardiol 2004; 43:25S-32S
34 Yasunobu Y, Oudiz R J, Sun X G, et al. End-tidal PCO2 abnormality and exercise limitation in patients with primary pulmonary hypertension. Chest 2005; 127:1637-1646
35 Methvin A B, Owens A T, Emmi A G, et al. Ventilatory inefficiency reflects right ventricular dysfunction in systolic heart failure. Chest 2011; 139:617-25
36 Matsumoto A, Itoh H, Eto Y, et al. End-tidal CO2 pressure decreases during exercise in cardiac patients:

association with severity of heart failure and cardiac output reserve. J Am Coll Cardiol 2000; 36:242-249

37 Tanabe Y, Hosaka Y, Ito M, et al. Significance of end-tidal P(CO(2)) response to exercise and its relation to functional capacity in patients with chronic heart failure. Chest 2001; 119:811-817

38 Hansen J E, Ulubay G, Chow B F, et al. Mixed-expired and end-tidal CO2 distinguish between ventilation and perfusion defects during exercise testing in patients with lung and heart diseases. Chest 2007; 132:977-983

39 Hemnes A R, Newman A L, Rosenbaum B, et al. Bedside end-tidal CO2 tension as a screening tool to exclude pulmonary embolism. Eur Respir J 2010; 35:735-741

40 Wilson R F, Beckman S B, Tyburski J G, et al. Pulmonary artery diastolic and wedge pressure relationships in critically ill and injured patients. Arch Surg 1988; 123:933-936

41 Her C, Cerabona T, Baek S H, et al. Increased pulmonary venous resistance in morbidly obese patients without daytime hypoxia: clinical utility of the pulmonary artery catheter. Anesthesiology 2010; 113:552-559

42 Lappas D, Lell W A, Gabel J C, et al. Indirect measurement of left-atrial pressure in surgical patients—pulmonary-capillary wedge and pulmonary-artery diastolic pressures compared with left-atrial pressure. Anesthesiology 1973; 38:394-397

43 Robbins I M, Newman J H, Johnson R F, et al. Association of the metabolic s3yndrome with pulmonary venous hypertension. Chest 2009; 136:31-36

44 Manual O. Operators Manual. NPB 75: Portable bedside capnograph/pulse oximeter. Pleasonton, CA: Nellcor Puritan Bennet, 1998

45 ATS statement: guidelines for the six-minute walk test. Am J Respir Crit Care Med 2002; 166:111-117

46 Provencher S, Sitbon O, Humbert M, et al. Long-term outcome with first-line bosentan therapy in idiopathic pulmonary arterial hypertension. Eur Heart J 2006; 27:589-595

47 Oudiz R J, Barst R J, Hansen J E, et al. Cardiopulmonary exercise testing and six-minute walk correlations in pulmonary arterial hypertension. Am J Cardiol 2006; 97:123-126

48 Hyduk A, Croft J B, Ayala C, et al. Pulmonary hypertension surveillance—United States, 1980-2002. MMWR Surveill Summ 2005; 54:1-28

What is claimed is:

1. A method for determining whether or not additional medical tests need to be conducted for a diagnosis of a pulmonary arterial hypertension condition in a patient, comprising the steps of:
   a) measuring end tidal carbon dioxide (EtCO2) of each of a plurality of oral expirations from the patient at rest with a system comprising:
      i) a housing;
      ii) a carbon dioxide analyzer located at least partially within the housing and adapted to measure the partial pressure of carbon dioxide in a composite gas;
      iii) a conduit adapted to transfer an expiration from the patient's mouth to the carbon dioxide analyzer;
      iv) a data transmitter adapted to transmit data from the carbon dioxide analyzer to a processor, the processor being located remotely from the housing and having a memory operably associated therewith;
      v) a range of carbon dioxide partial pressure values stored in the memory; and
      vi) an indicator adapted to respond to a signal from the processor to provide an output in a human cognizable format;
   b) calculating a composite EtCO2 value for the plurality of oral expirations at rest;
   c) comparing the composite EtCO2 value to the range of carbon dioxide partial pressure values stored in the memory of the system;
   d) generating a first signal based upon the comparison in step (c), the first signal indicative of whether or not additional medical tests needs to be conducted for the diagnosis of pulmonary arterial hypertension, wherein a lower range of the composite EtCO2 value is indicative of pulmonary arterial hypertension; and
   e) transmitting the first signal to the indicator of the system.

2. The method of claim 1, wherein each of the plurality of oral expirations from the patient are captured using a tube placed in a mouth of the patient.

3. The method of claim 1, further comprising instructing the patient to breathe tidally into a plastic tube inserted into a mouth of the patient.

4. The method of claim 1, further comprising calibrating the carbon dioxide analyzer for a precision of ±2 mm Hg up to 38 mm Hg for a partial pressure of carbon dioxide.

5. The method of claim 1, further comprising calibrating the carbon dioxide analyzer for a precision of ±0.08% for every 1 mm Hg over 40 mm Hg for a partial pressure of carbon dioxide.

6. The method of claim 1, further comprising
   administering a 6-minute walking distance test (6MWT) check to at least one patient for further diagnosis of pulmonary arterial hypertension; and
   diagnosing pulmonary arterial hypertension when the EtCO2 does not increase after the 6MWT check.

7. The method of claim 6, further comprising administering the 6MWT after the at least one patient has received a therapy for the pulmonary arterial hypertension.

8. A method for determining whether or not additional medical tests need to be conducted for a diagnosis of a pulmonary arterial hypertension condition in a patient, comprising the steps of:
   a) measuring end tidal carbon dioxide (EtCO2) of each of a plurality of oral expirations from the patient at rest with a system comprising:
      i) a housing;
      ii) a carbon dioxide analyzer located at least partially within the housing and adapted to measure the partial pressure of carbon dioxide in a composite gas;
      iii) a conduit adapted to transfer an expiration from the patient's mouth to the carbon dioxide analyzer;
      iv) a data transmitter adapted to transmit data from the carbon dioxide analyzer to a processor, the processor being located remotely from the housing and having a memory operably associated therewith;
      v) a range of carbon dioxide partial pressure values stored in the memory; and
      vi) an indicator adapted to respond to a signal from the processor to provide an output in a human cognizable format;
   b) calculating a composite EtCO2 value for the plurality of oral expirations at rest;
   c) comparing the composite EtCO2 value to the range of carbon dioxide partial pressure values stored in the memory of the system;
   d) generating a first signal based upon the comparison in step (c), the first signal indicative of whether or not additional medical tests needs to be conducted for the diagnosis of pulmonary arterial hypertension, wherein a lower range of the composite EtCO2 value is indicative of pulmonary arterial hypertension and a higher range of the composite EtCO2 value is indicative of pulmonary venous hypertension; and e) transmitting the first signal to the indicator of the system.

9. A method for determining whether or not additional medical tests need to be conducted for a diagnosis of a pulmonary arterial hypertension condition in a patient, comprising the steps of:
   a) measuring end tidal carbon dioxide (EtCO2) of each of a plurality of oral expirations from the patient at rest with a device comprising:
      i) a housing;
      ii) a carbon dioxide analyzer located at least partially within the housing and adapted to measure the partial pressure of carbon dioxide in a composite gas;
      iii) a conduit adapted to transfer an expiration from the patient's mouth to the carbon dioxide analyzer;
      iv) a first processor located within the housing and having a memory operably associated therewith;
      v) a range of carbon dioxide partial pressure values stored in the memory; and
      vi) an indicator adapted to respond to a signal from the processor to provide an output in a human cognizable format;
   b) calculating a composite EtCO2 value for the plurality of oral expirations at rest
   c) comparing the composite EtCO2 value to the range of carbon dioxide partial pressure values stored in the memory of the device;
   d) generating a first signal based upon the comparison in step (c), the first signal indicative of whether or not additional medical tests needs to be conducted for the diagnosis of pulmonary arterial hypertension, wherein a lower range of the composite EtCO2 value is indicative of pulmonary arterial hypertension; and
   e) transmitting the first signal to the indicator of the device.

10. The method of claim 9, wherein each of the plurality of oral expirations from the patient are captured using a tube placed in a mouth of the patient.

11. The method of claim 9, further comprising instructing the patient to breathe tidally into a plastic tube inserted into a mouth of the patient.

12. The method of claim 9, further comprising calibrating the carbon dioxide analyzer for a precision of ±2 mm Hg up to 38 mm Hg for a partial pressure of carbon dioxide.

13. The method of claim 9, further comprising calibrating the carbon dioxide analyzer for a precision of ±0.08% for every 1 mm Hg over 40 mm Hg for a partial pressure of carbon dioxide.

14. The method of claim 9, further comprising
   administering a 6-minute walking distance test (6MWT) check to at least one patient for further diagnosis of pulmonary arterial hypertension; and
   diagnosing pulmonary arterial hypertension when the EtCO2 does not increase after the 6MWT check.

15. the method of claim 14, further comprising administering the 6MWT after the at least one patient has received a therapy for the pulmonary arterial hypertension.

16. A method for determining whether or not additional medical tests need to be conducted for a diagnosis of a pulmonary arterial hypertension condition in a patient, comprising the steps of:
   a) measuring end tidal carbon dioxide (EtCO2) of each of a plurality of oral expirations from the patient at rest with a device comprising:
      i) a housing;
      ii) a carbon dioxide analyzer located at least partially within the housing and adapted to measure the partial pressure of carbon dioxide in a composite gas;
      iii) a conduit adapted to transfer an expiration from the patient's mouth to the carbon dioxide analyzer;
      iv) a first processor located within the housing and having a memory operably associated therewith;
      v) a range of carbon dioxide partial pressure values stored in the memory; and
      vi) an indicator adapted to respond to a signal from the processor to provide an output in a human cognizable format;
   b) calculating a composite EtCO2 value for the plurality of oral expirations at rest;
   c) comparing the composite EtCO2 value to the range of carbon dioxide partial pressure values stored in the memory of the device;
   d) generating a first signal based upon the comparison in step (c), the first signal indicative of whether or not additional medical tests needs to be conducted for the diagnosis of pulmonary arterial hypertension, wherein a lower range of the composite EtCO2 value is indicative of pulmonary arterial hypertension and a higher range of the composite EtCO2 value is indicative of pulmonary venous hypertension; and
   e) transmitting the first signal to the indicator of the device.

* * * * *

UNITED STATES PATENT AND TRADEMARK OFFICE
CERTIFICATE OF CORRECTION

PATENT NO. : 9,687,176 B2
APPLICATION NO. : 13/448095
DATED : June 27, 2017
INVENTOR(S) : Anna R. Hemnes et al.

It is certified that error appears in the above-identified patent and that said Letters Patent is hereby corrected as shown below:

On the Title Page

On the page 2, in Column 1, under "Other Publications", Line 44, delete ""latory" and insert -- "History --, therefor.

On the page 2, in Column 1, under "Other Publications", Line 44, delete ""Ineffi ciency" and insert -- Inefficiency --, therefor.

On the page 2, in Column 1, under "Other Publications", Line 44, delete "Refl ects" and insert -- Reflects --, therefor.

In the Specification

In Column 2, Lines 43-44, after "making" insert -- . --.

In Column 6, Line 60, delete "$EtCO_22$" and insert -- $EtCO_2$ --, therefor.

In Column 11, Line 22, delete "$EtCo_2$" and insert -- $EtCO_2$ --, therefor.

In Column 12, Line 32, delete "scanning" and insert -- scanning. --, therefor.

In Column 13, Line 24, delete "markings" and insert -- markings. --, therefor.

In Column 19, Line 44, delete "weaning" and insert -- weaning. --, therefor.

In Column 19, Line 48, delete "C02" and insert -- CO2 --, therefor.

In Column 26, Line 44, before "38 mmHg" insert -- $\leq$ --.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*